US011511093B2

(12) United States Patent
Shin et al.

(10) Patent No.: US 11,511,093 B2
(45) Date of Patent: Nov. 29, 2022

(54) GASTRORETENTIVE DRUG DELIVERY DEVICE HAVING EXPANDABLE STRUCTURE AND MANUFACTURING METHOD THEREFOR

(71) Applicants: WONKWANG UNIVERSITY CENTER FOR INDUSTRY ACADEMY COOPERATION, Jeollabuk-do (KR); RESEARCH & BUSINESS FOUNDATION SUNGKYUNKWAN UNIVERSITY, Gyeonggi-do (KR)

(72) Inventors: Soyoung Shin, Jeollabuk-do (KR); Beom Soo Shin, Seoul (KR); Seung Eun Chung, Gyeonggi-do (KR); Meoung Jun Park, Gyeonggi-do (KR)

(73) Assignees: WONKWANG UNIVERSITY CENTER FOR INDUSTRY ACADEMY COOPERATION, Jeollabuk-Do (KR); RESEARCH & BUSINESS FOUNDATION SUNGKYUNKWAN UNIVERSITY, Gyeonggi-Do (KR)

( * ) Notice: Subject to any disclaimer, the term of this patent is extended or adjusted under 35 U.S.C. 154(b) by 247 days.

(21) Appl. No.: 17/030,064

(22) Filed: Sep. 23, 2020

(65) Prior Publication Data
US 2021/0106799 A1    Apr. 15, 2021

(30) Foreign Application Priority Data

Oct. 11, 2019  (KR) .................. 10-2019-0126409
May 18, 2020  (KR) .................. 10-2020-0058892

(51) Int. Cl.
*A61M 31/00*  (2006.01)
*A61K 9/00*  (2006.01)

(52) U.S. Cl.
CPC ......... *A61M 31/002* (2013.01); *A61K 9/0065* (2013.01); *A61M 2205/106* (2013.01); *A61M 2207/00* (2013.01); *A61M 2210/1053* (2013.01)

(58) Field of Classification Search
CPC ........ A61M 31/002; A61M 2210/1053; A61M 2205/0216; A61M 5/16804; A61M 5/172;
(Continued)

(56) References Cited

U.S. PATENT DOCUMENTS 4,735,804 A   4/1988  Caldwell et al.
4,767,627 A   8/1988  Caldwell et al.
(Continued)

FOREIGN PATENT DOCUMENTS

KR   1020030023876 A   3/2003
KR   1020090004280 A   1/2009
(Continued)

OTHER PUBLICATIONS

P.L. Bardonnet, et al., "Gastroretentive dosage forms: Overview and special case of Helicobacter pylori", Journal of Controlld Release, vol. 111, Issues 1-2, Mar. 10, 2006, pp. 1-18.

*Primary Examiner* — Nicholas J. Weiss
*Assistant Examiner* — Linnae E. Raymond
(74) *Attorney, Agent, or Firm* — Tarolli, Sundheim, Covell & Tummino LLP

(57) ABSTRACT

The present disclosure provides a gastroretentive drug delivery device having an expandable structure. The drug delivery device includes: a capsule body; an arm moving part movable within the capsule body; an elastic body positioned between one end of the capsule body and the arm moving part and acting to move the arm moving part toward the other end of the capsule body; an arm support part movable within the capsule body; a capsule cap configured to engage
(Continued)

the other end of the capsule body; a rail formed within the capsule body; and an arm configured to be unfolded by longitudinal movement of the arm moving part and move along the rail. A disintegrable immediate-release formulation is positioned between the arm moving part and the arm support part. A disintegrable sustained-release formulation is positioned between the arm support part and the capsule cap.

16 Claims, 19 Drawing Sheets

(58) Field of Classification Search
CPC .. A61M 5/16836; A61M 5/168; A61M 31/00; A61K 9/0065; A61K 9/00; A61K 9/0004; A61K 9/0053; A61J 3/07; A61J 3/00; A61D 7/00; A61B 5/6861; A61B 2562/162

See application file for complete search history.

(56) References Cited

U.S. PATENT DOCUMENTS

| | | |
|---|---|---|
| 8,298,574 B2 | 10/2012 | Tsabari et al. |
| 2021/0370033 A1* | 12/2021 | Menachem .......... A61K 9/0065 |
| 2022/0142566 A1* | 5/2022 | Huang .................. A61M 31/00 |

FOREIGN PATENT DOCUMENTS

| | | | | |
|---|---|---|---|---|
| KR | 20100001230 A | * | 1/2010 | ......... A61B 1/00071 |
| KR | 101268215 B1 | | 5/2013 | |
| KR | 101269829 31 | | 5/2013 | |

* cited by examiner

[FIG. 1]
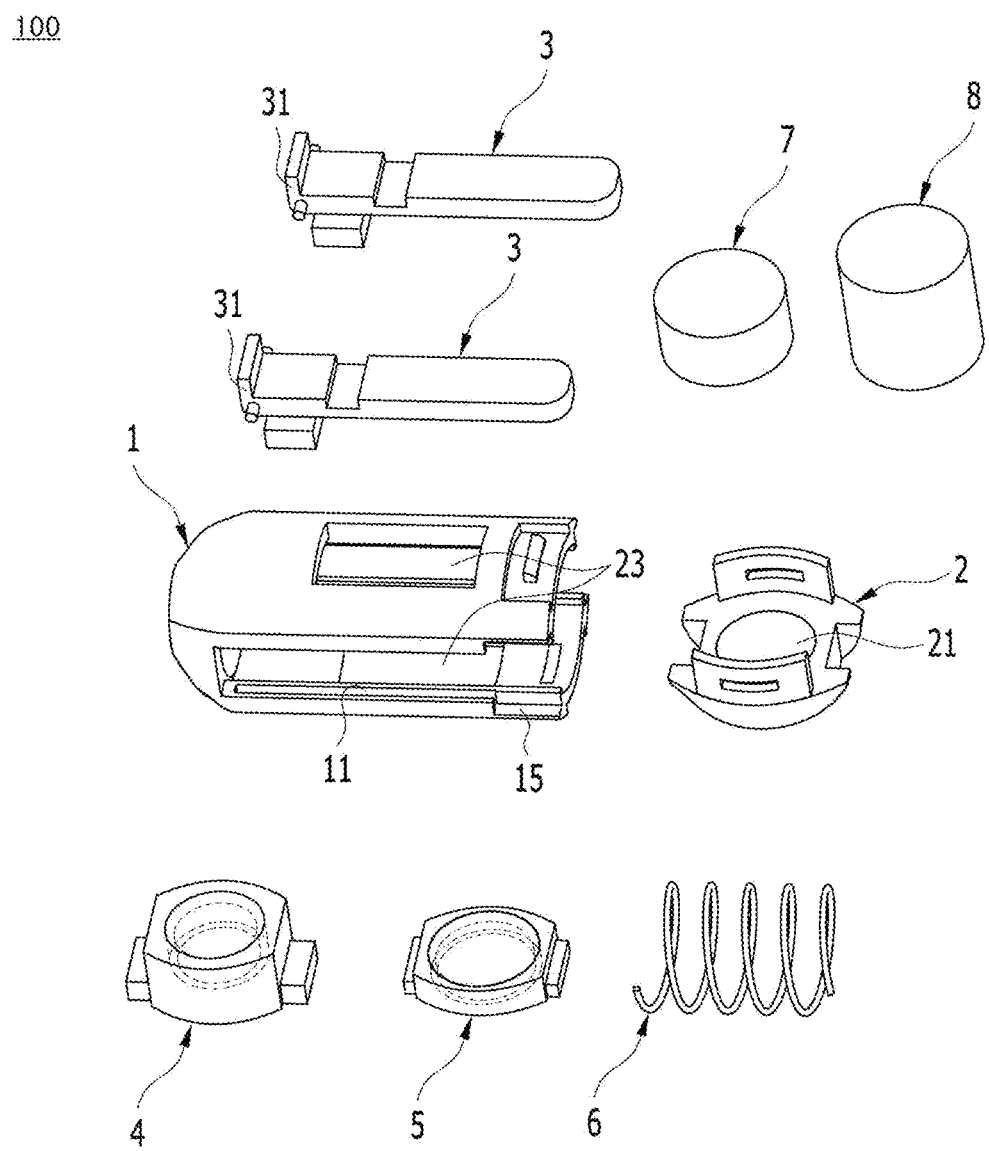

[FIG. 2]
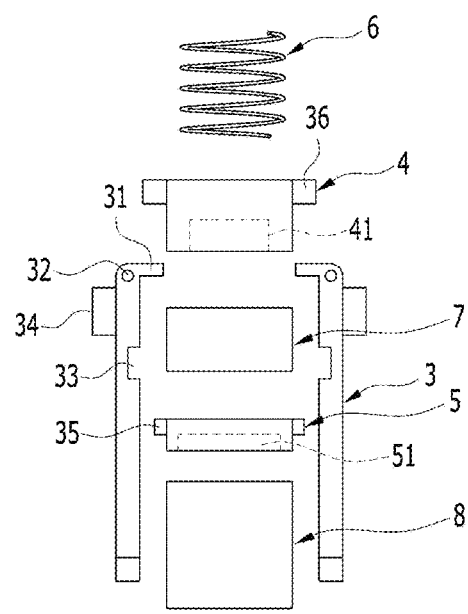

[FIG. 3A]
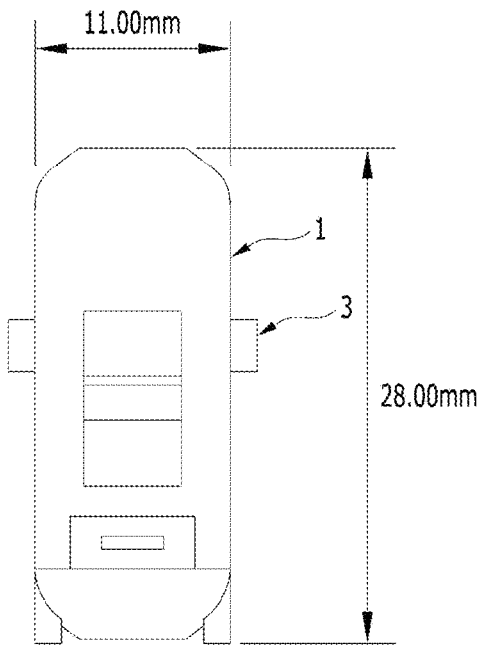
[FIG. 3B]
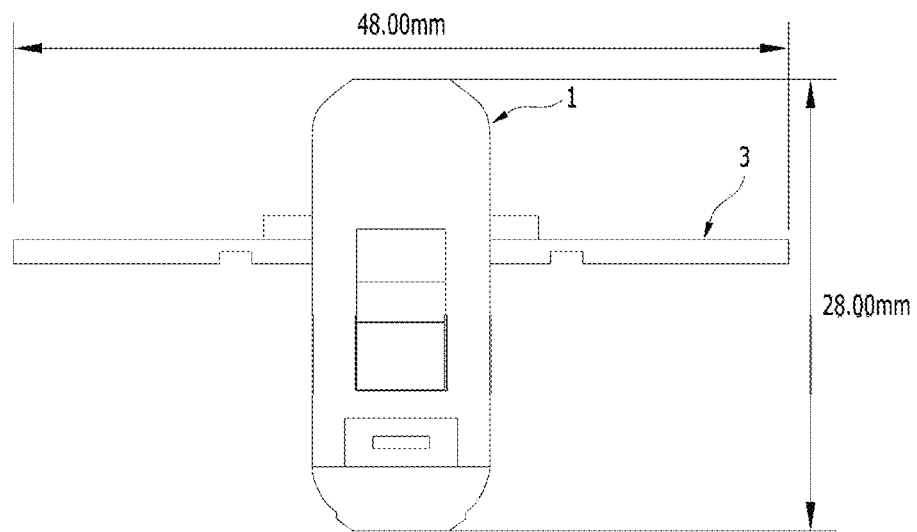

[FIG. 4A]
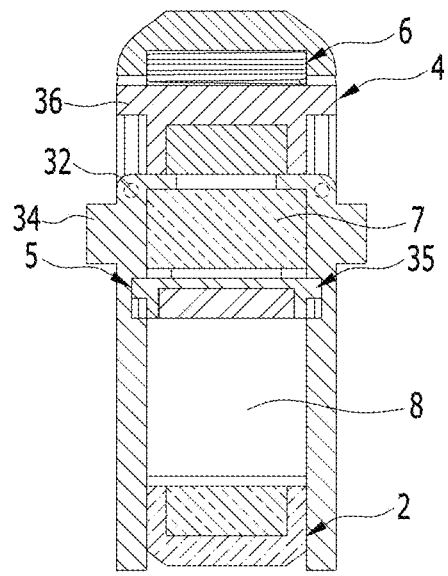
[FIG. 4B]
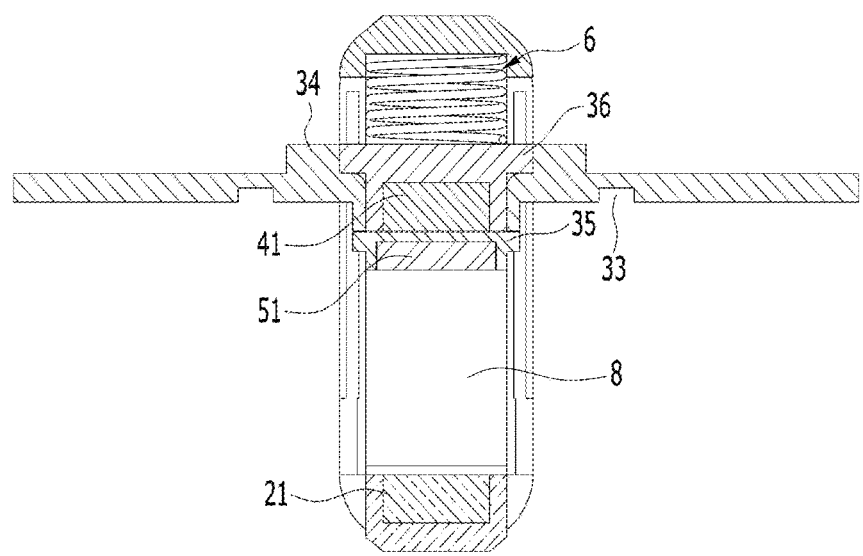

[FIG. 5A]
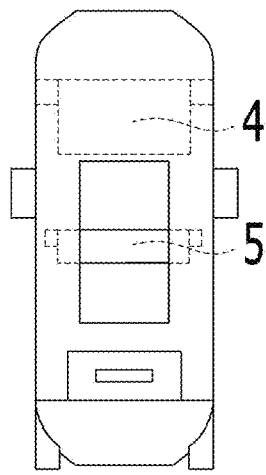
[FIG. 5B]
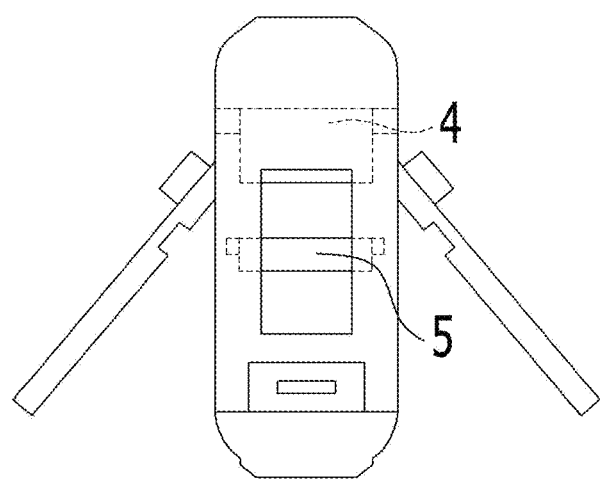

[FIG. 5C]
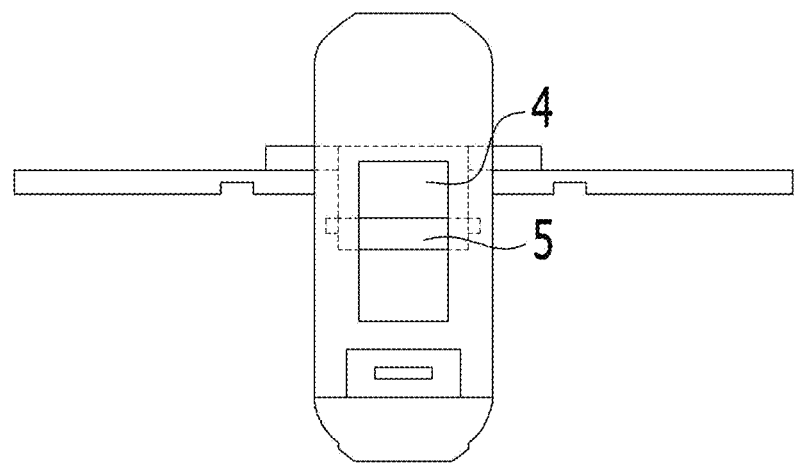
[FIG. 5D]
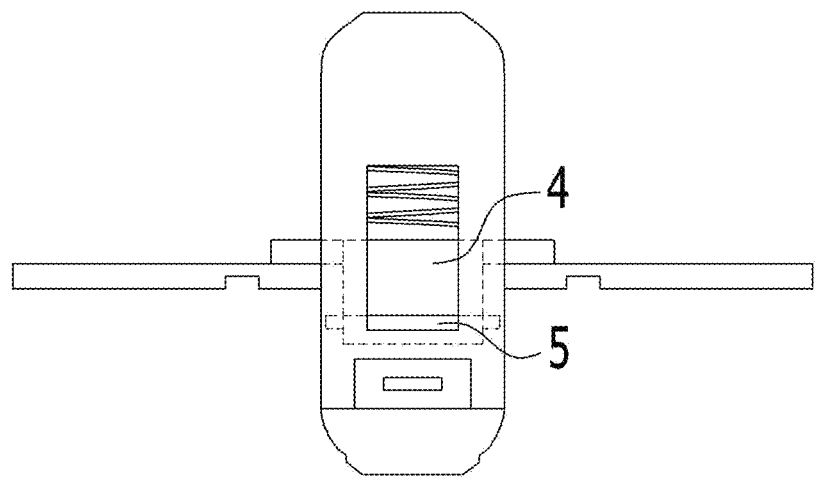

[FIG. 5E]
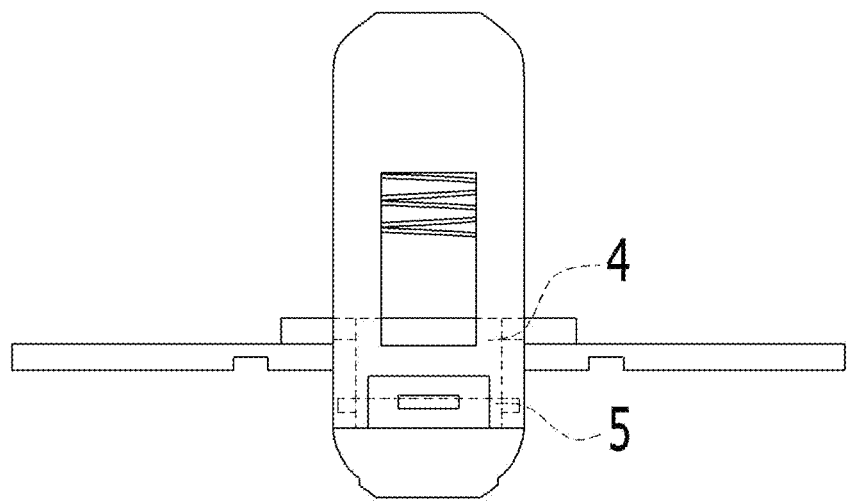
[FIG. 5F]
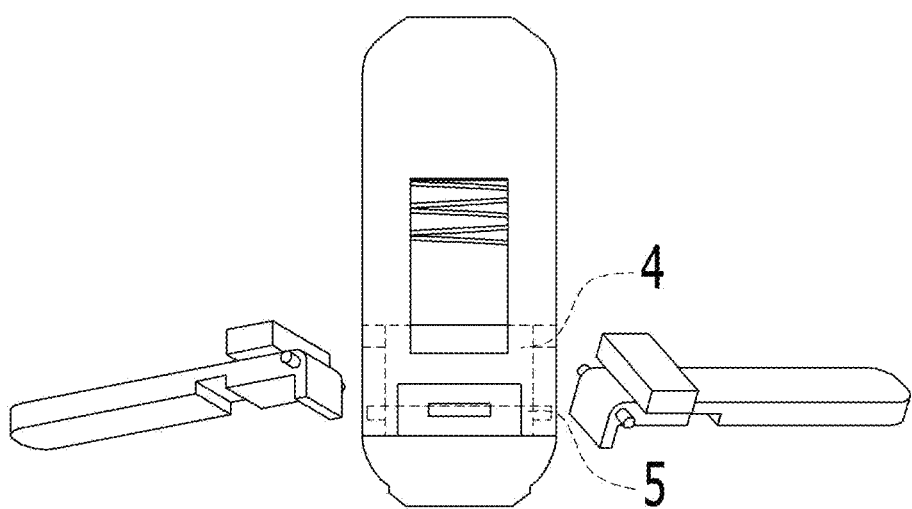

[FIG. 6A]
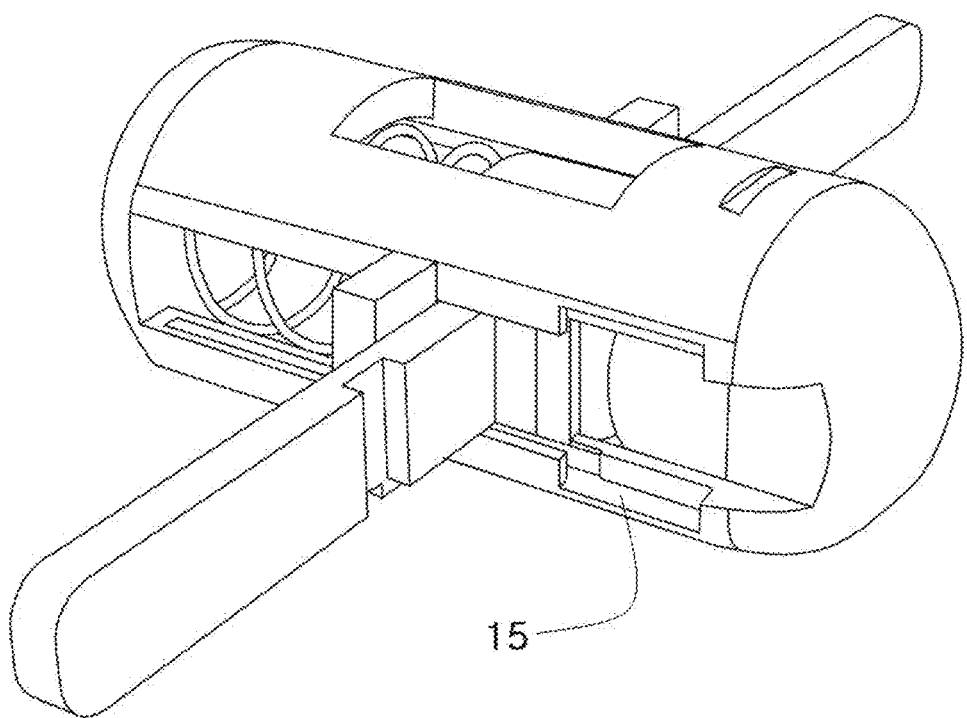

[FIG. 6B]
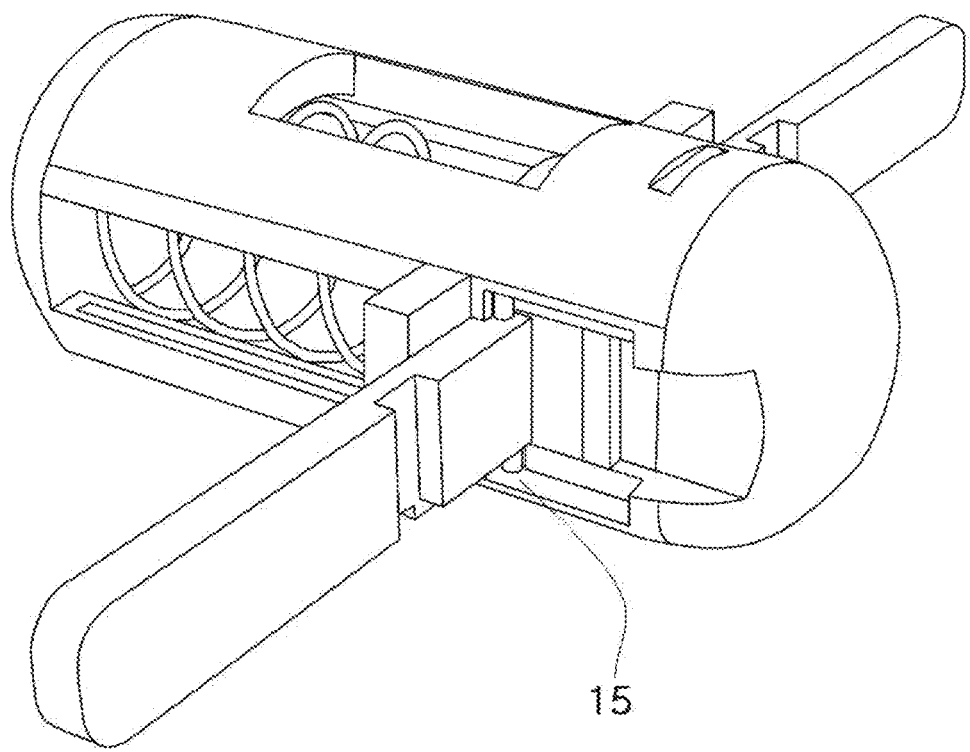

[FIG. 6C]
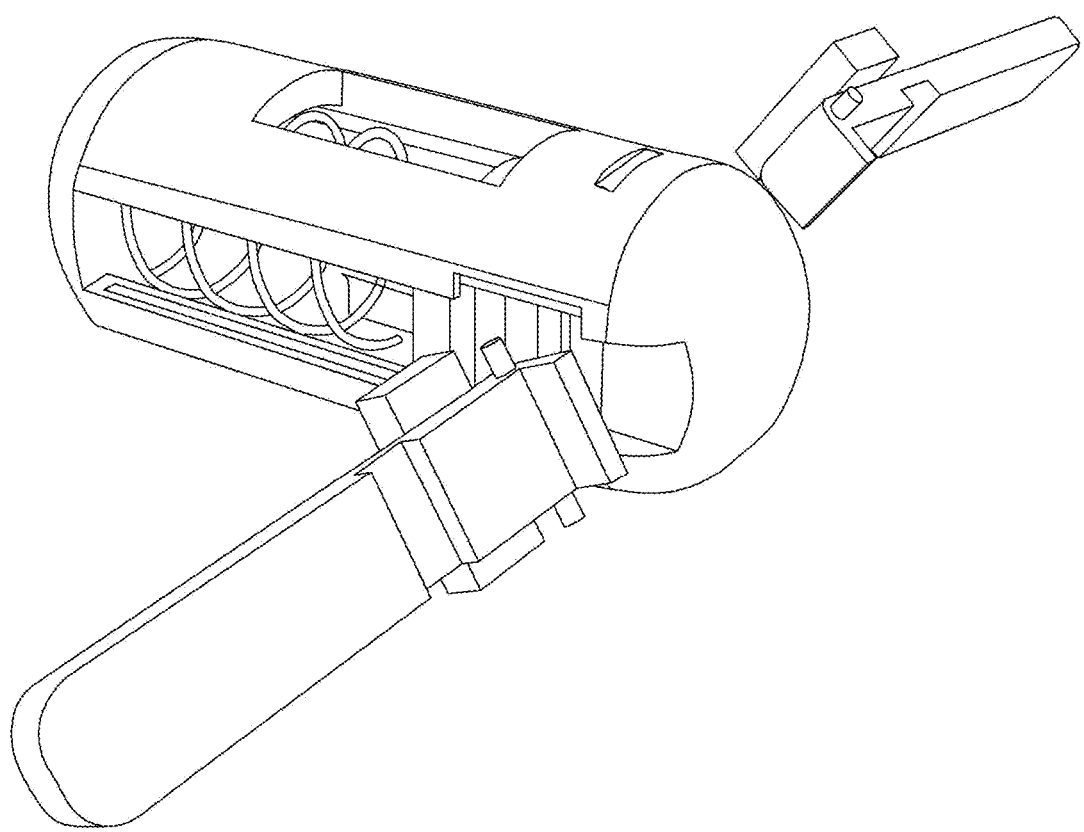

[FIG. 7]
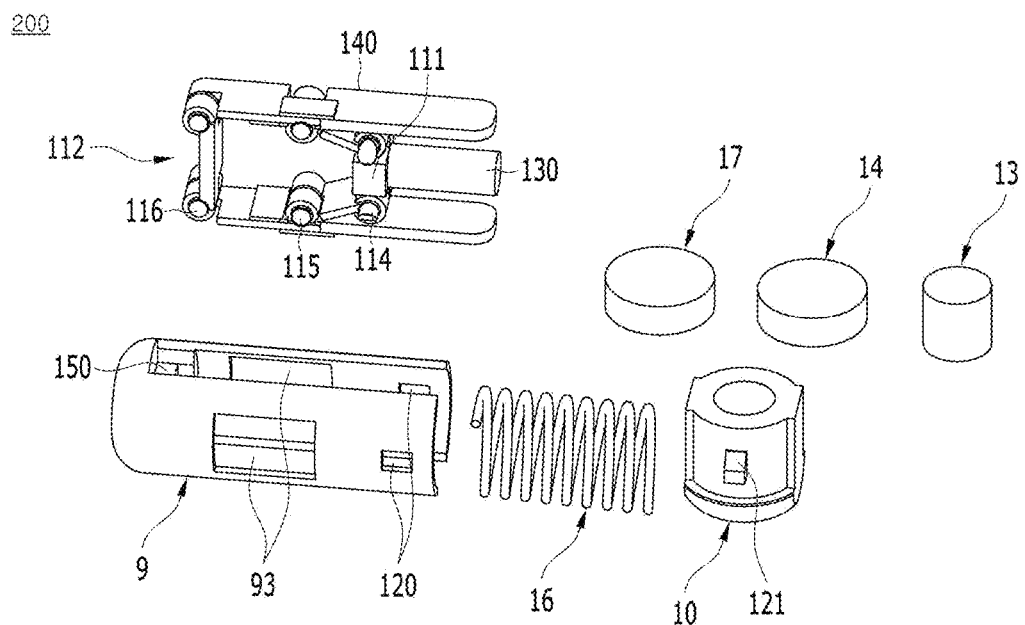
[FIG. 8A]
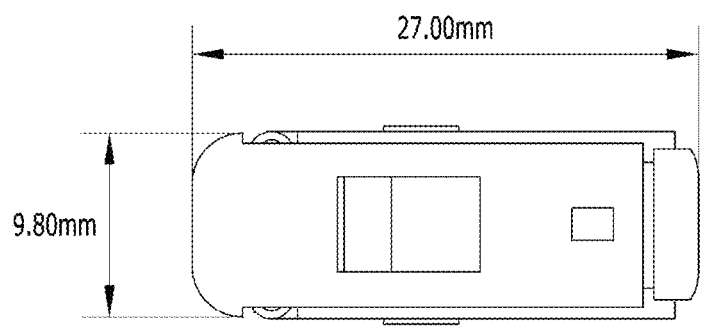

[FIG. 8B]
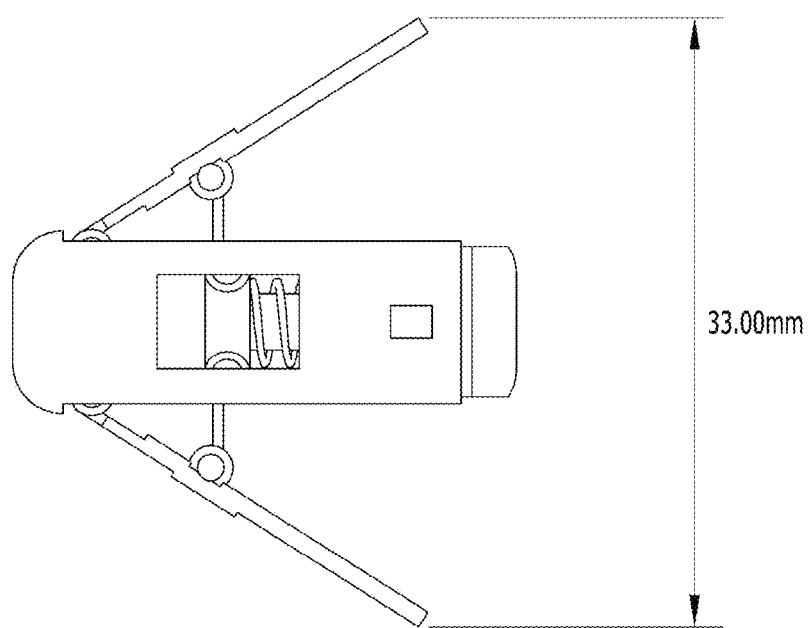

[FIG. 9]
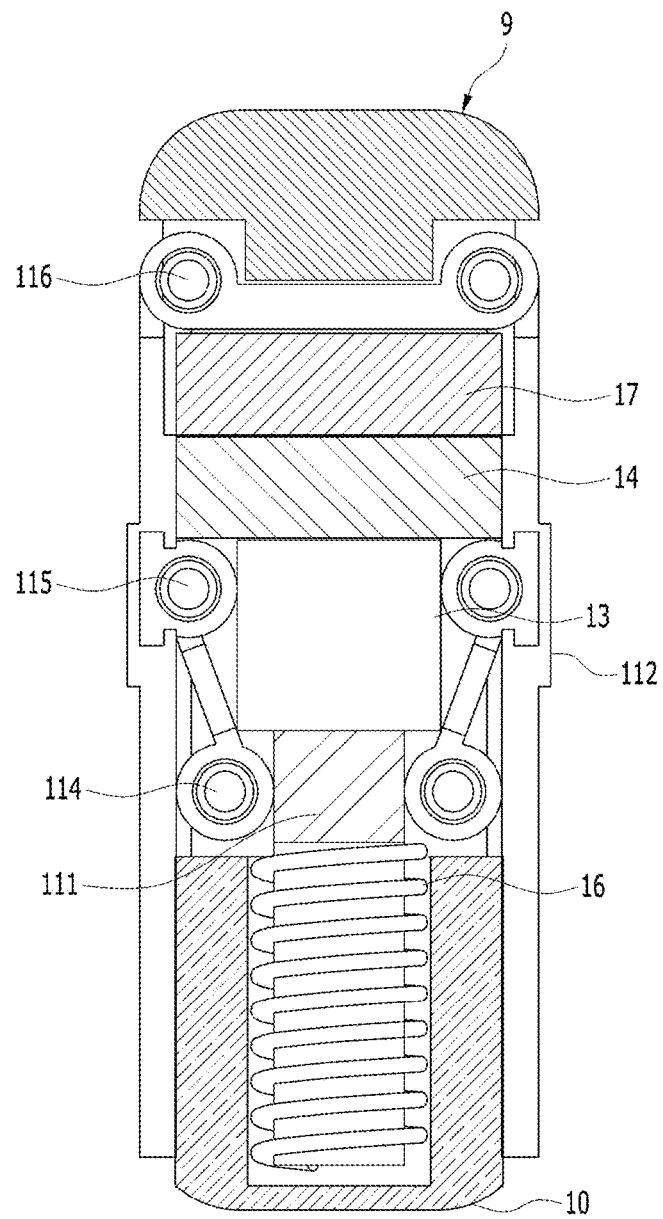

[FIG. 10A]
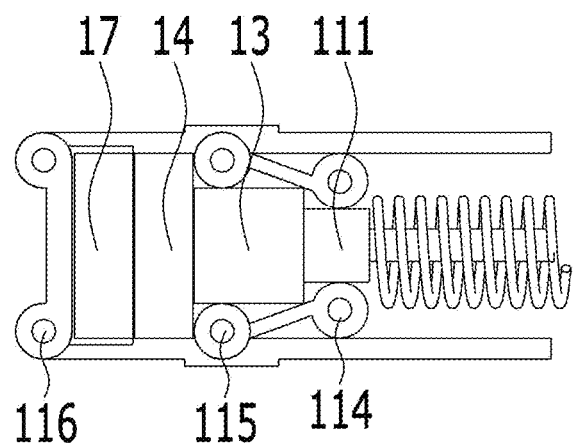
[FIG. 10B]
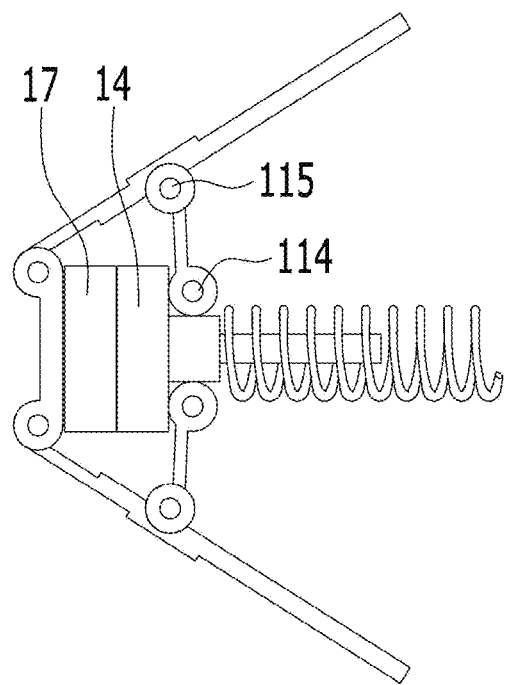

[FIG. 10C]
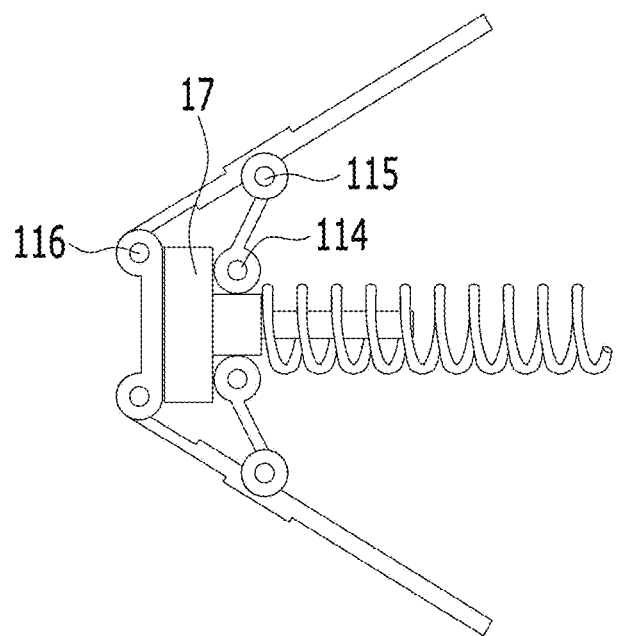
[FIG. 10D]
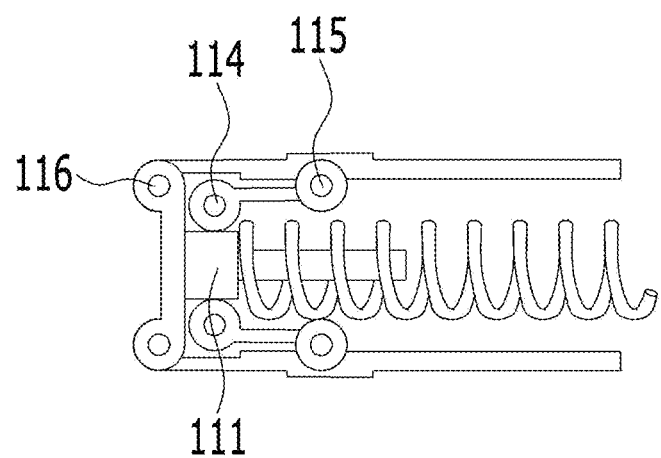

[FIG. 11]
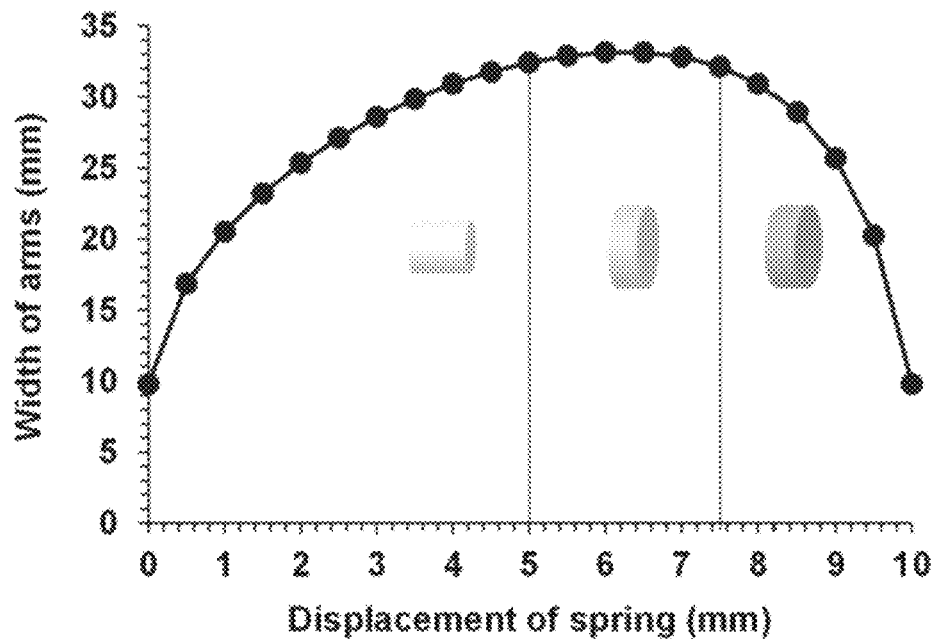
[FIG. 12]
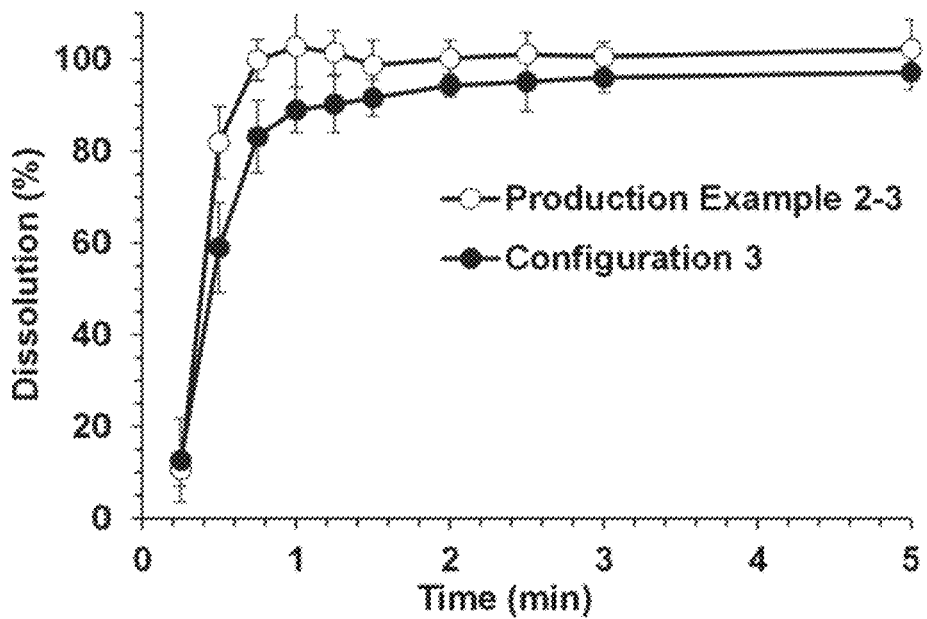

[FIG. 13]
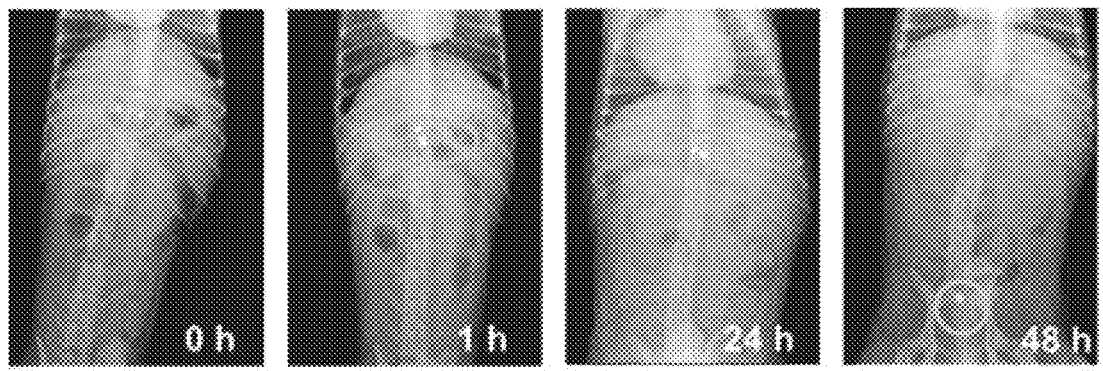
[FIG. 14]
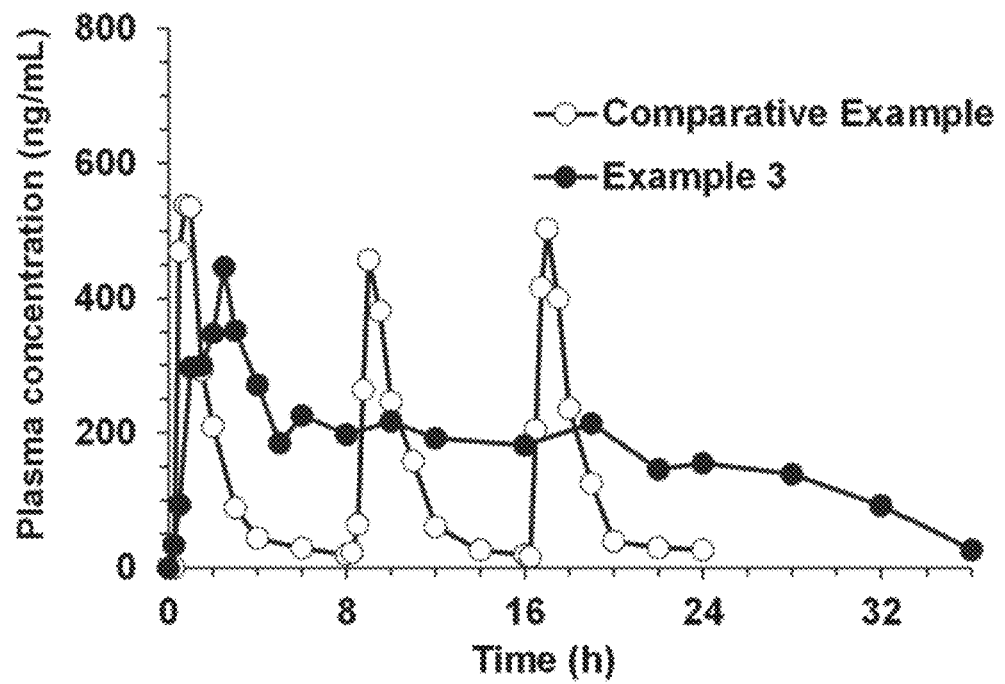

[FIG. 15]
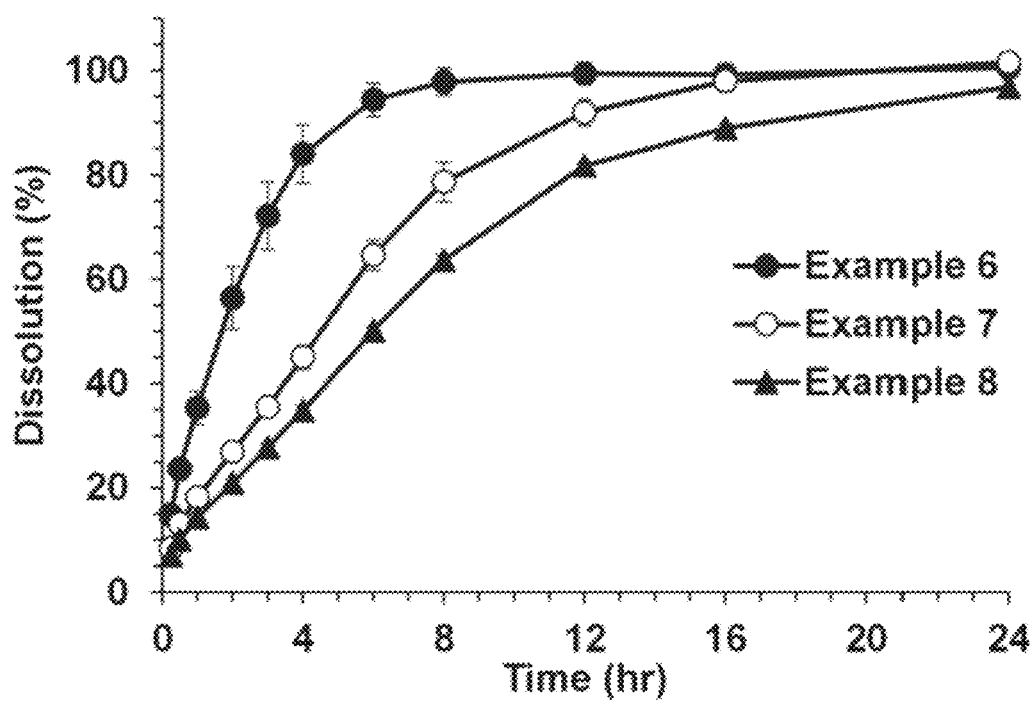

[FIG. 16]
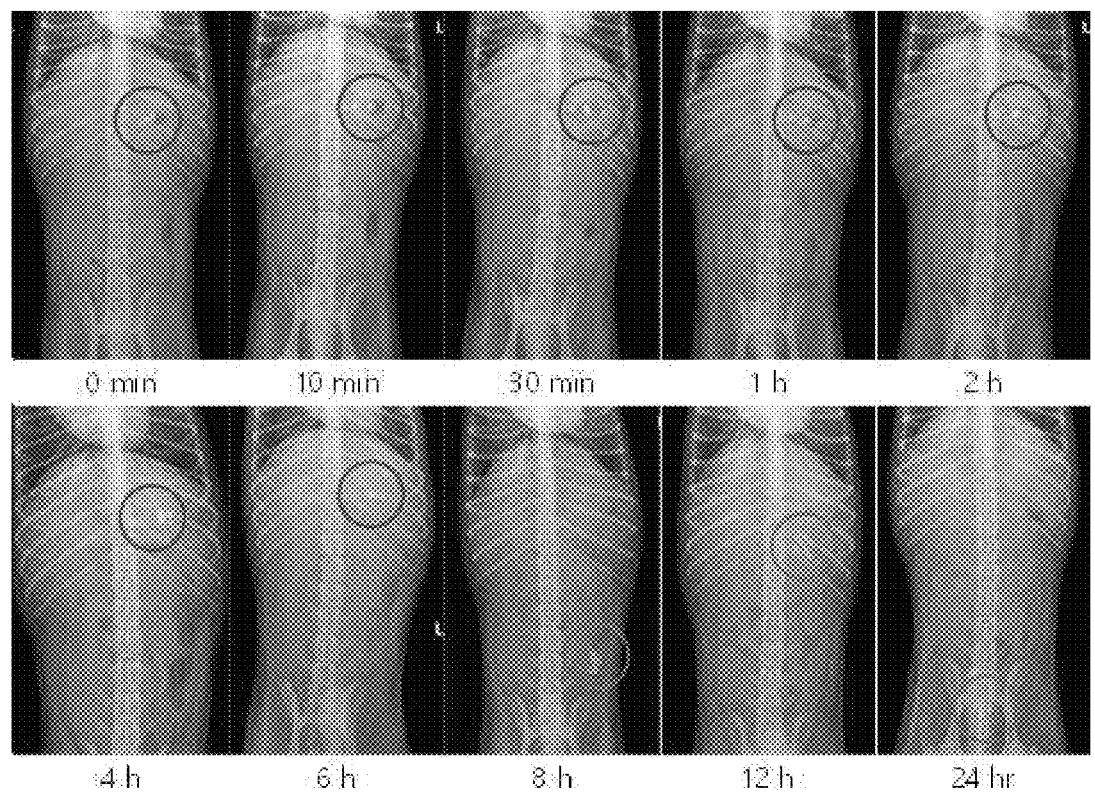

GASTRORETENTIVE DRUG DELIVERY DEVICE HAVING EXPANDABLE STRUCTURE AND MANUFACTURING METHOD THEREFOR

CROSS-REFERENCE TO RELATED APPLICATION(S)

This application claims priority to Korean Patent Application No. 10-2019-0126409, filed on Oct. 11, 2019, and Korean Patent Application No. 10-2020-0058892, filed on May 18, 2020, the disclosure of which is incorporated herein by reference in its entirety.

BACKGROUND

Technical Field

The present disclosure relates to a gastroretentive drug delivery device having an expandable structure and a manufacturing method therefor, and more particularly, to a gastroretentive drug delivery device, which uses the change in shape of an arm structure resulting from the disintegration and dissolution of an immediate-release portion and a sustained-release portion, and a manufacturing method therefor.

Description of the Related Art

A gastroretentive drug delivery system is a drug delivery system which allows a formulation to release a drug continuously while remaining in the stomach for a long time. When the gastroretentive drug delivery system is applied to various drugs, such as a drug whose absorption is limited to the upper gastrointestinal tract, a drug which is degraded at the high pH of the small intestine, or a drug that acts in the stomach, it is possible to improve the bioavailability of the drug, reduce the frequency of taking the drug and thus improve patient's drug compliance, and increase the therapeutic effect of the drug.

Previously, various technologies have been attempted to develop gastroretentive drug delivery systems. These technologies are classified into a sinking system that sinks to the bottom of the stomach due to its higher density than gastric juice, a floating system that floats in gastric juice due to its lower density than gastric juice, an expanding system that swells or expands in the stomach, and a mucoadhesive system that adheres to the gastrointestinal mucosa (Bardonnet et al., 2006). Among them, the expanding system is a drug delivery system that cannot pass through the pylorus of the stomach due to the increased size thereof resulting from swelling or expansion of the structure thereof in the stomach, and remains in the stomach until the size thereof becomes small enough to pass through the pylorus. Therefore, the expandable gastroretentive drug delivery system has advantages in that it is less affected by other factors, such as the state of gastric juice and mucosa, gastrointestinal tract movements, and the presence of food, compared to the floating system, the sinking system, and the mucoadhesive system, and can be maintained in a gastric retention state.

For example, Korean Patent Application Publication Nos. 10-2003-0023876 and 10-2009-0004280 and Korean Patent Nos. 1269829 and 1268215 disclose matrix-type sustained-release oral formulations that achieve gastric retention either by using a swellable polymer that swells in the stomach or by containing the swellable polymer and a bubble-generating agent together. Meanwhile, U.S. Pat. Nos. 4,735,804, 4,767,627 and 8,298,574 disclose expandable drug delivery systems for oral administration in which various forms of compressed structures containing pharmacologically active drugs are packaged in containers such as capsules.

However, such conventional expandable gastroretentive drug delivery systems have problems in that, since they delay gastric retention of the formulation depending on a specific polymer material having the property of swelling in the stomach, they are affected by the properties of the polymer added and the stomach's internal environment, and processes for producing them are also complicated. The gastroretentive drug delivery system based on the swellable polymer has a problem in that, since the polymer takes time to swell, the formulation moves to the small intestine without remaining in the stomach for a sufficient period of time. In addition, in most cases, the drug delivery system has a limitation in that it moves to the small intestine through the pylorus before drug release is completed, while the size of the drug delivery system decreases as drug release proceeds. Furthermore, most of the conventional gastroretentive drug delivery systems have a limitation in that, since the prescription and form of the formulation need to vary depending on the drug to be applied, it takes a long time to develop the drug delivery systems and the types of drug that can be applied are limited.

SUMMARY

An object of the present disclosure is to provide an expandable gastroretentive drug delivery device independent of drug release characteristics and gastric retention characteristics in order to overcome the limitations of the conventional expandable gastroretentive drug delivery system. In addition, another object of the present disclosure is to provide an expandable gastroretentive drug delivery device, which is capable of expanding rapidly when delivered into the stomach and is capable of retaining gastric retention ability until the time when drug release is completed.

According to the present disclosure, while an immediate-release formulation containing a pharmacologically active drug in a gastroretentive drug delivery device is disintegrated, the drug delivery device remains in the stomach by expansion as the arm thereof is unfolded. A sustained-release formulation included in the drug delivery device releases the pharmacologically active drug slowly into the stomach, and when release of the drug from the sustained-release formulation is completed, the unfolded arm structure is finally detached or folded again, so that the drug delivery device loses gastric retention ability, is removed from the stomach, and moves to the small intestine. According to this expandable gastroretentive drug delivery device, the expansion initiation time at which the arm is unfolded and the time at which the drug reaches the initial effective blood concentration may be determined by the disintegration and dissolution rates of the immediate-release formulation contained in the device. In addition, this expandable gastroretentive drug delivery device enables drug release in the stomach for a desired period by adjusting the expansion maintenance time of the drug delivery device and the duration of release of the drug based on the disintegration and dissolution rates of the sustained-release formulation.

The problem to be solved by the present disclosure is not limited to the problem(s) mentioned above, and another problem(s) that is (are) not mentioned may be clearly understood by those skilled in the related art from the following description.

A gastroretentive (GR) drug delivery device having an expandable structure according to one embodiment of the present disclosure may include: a capsule device having gastric retention ability; and an immediate-release (IR) formulation and a sustained-release (SR) formulation, which are included in the capsule device and contain a pharmacologically active component. The immediate-release formulation may contain a physiologically active component and a component that disintegrates the formulation quickly. The sustained-release formulation may contain a physiologically active component and a component that delays release of the physiologically active component. The capsule device may include a structure that enables the arm to be unfolded by disintegration of the immediate-release formulation and the arm to be detached or folded by disintegration of the sustained-release formulation.

In addition, a method for producing a gastroretentive drug delivery device having an expandable structure according to one embodiment of the present disclosure may include steps of: producing a capsule device; producing a pharmaceutical composition that releases a pharmacologically active component and controls the expandability of the capsule device; and assembling the capsule device, and filling the capsule device with the pharmaceutical composition, followed by sealing.

A gastroretentive drug delivery device according to one embodiment of the present disclosure may include: a capsule body having a space formed therein; an arm moving part movable along the longitudinal direction within the capsule body; an elastic body positioned between one end of the capsule body and the arm moving part and acting to move the arm moving part in the longitudinal direction toward the other end of the capsule body; an arm support part movable along the longitudinal direction within the capsule body; a capsule cap configured to engage the other end of the capsule body; a rail formed along the longitudinal direction within the capsule body; and an arm configured to be unfolded by longitudinal movement of the arm moving part and to move along the rail. A disintegrable immediate-release formulation is positioned between the arm moving part and the arm support part, and a disintegrable sustained-release formulation is positioned between the arm support part and the capsule cap.

In addition, the arm may include a rotating part extending from one end thereof, and the arm may be unfolded by rotation with respect to the rotating part by longitudinal movement of the arm moving part.

In addition, the arm moving part may rotate the arm while moving in the longitudinal direction toward the arm support part by disintegration of the immediate-release formulation, and the arm may be unfolded perpendicularly to the capsule body when the arm moving part comes into contact with the arm support part by complete disintegration of the immediate-release formulation.

In addition, the contacted arm moving part and arm support part may move the unfolded arm along the rail while moving in the longitudinal direction toward the capsule cap by disintegration of the sustained-release formulation, and the arm may reach a portion free of the rail by complete disintegration of the sustained-release formulation and may be detached from the capsule body.

In addition, each of the arm moving part, the arm support part and the capsule cap may include a magnetic material for generating mutual attraction.

In addition, the arm moving part may move in the longitudinal direction toward the arm support part by the elastic force from the elastic body and the attraction between the arm moving part and the arm support part upon disintegration of the immediate-release formulation, and the arm support part may move in the longitudinal direction toward the capsule cap by the attraction between the arm support part and the capsule cap upon disintegration of the sustained-release formulation.

In addition, the gastroretentive drug delivery device may further include one or more drug release windows formed in the capsule body. The drug release windows may be a pair of windows facing each other, which may be formed in the capsule body.

In addition, the rotating part of the arm may include a rotating shaft. The arm may be unfolded by rotation with respect to the rotating shaft by longitudinal movement of the arm moving part, and then may move along the rail through the rotating part.

In addition, the arm may include a groove, and the arm support part may include an extension formed to fit into the groove.

In addition, the arm moving part may include a bidirectional extension on a lateral side thereof facing the elastic body. The extension of the arm moving part may come into contact with the rotating part of the perpendicularly unfolded arm through the lower end of the extension, so that the arm may be maintained in the perpendicularly unfolded state.

In addition, the arm may include an extension formed on the outside thereof so as to be adjacent to the end from which the rotating part extends. The extension of the arm may come into contact with the outside of the extension of the arm moving part in a state in which the arm is unfolded perpendicularly, so that the arm may be maintained in the perpendicularly unfolded state.

In addition, the rail may be composed of a pair of rails formed within the capsule body, and the arm may be a pair of arms, which are fitted into the rails, respectively, and connected to the capsule body.

In addition, the rail may be composed of two or more pairs of rails formed within the capsule body, and the arm may be composed of two or more pairs of arms, which are fitted into the pairs of rails, respectively, and connected to the capsule body.

A method for manufacturing a gastroretentive drug delivery device according to one embodiment of the present disclosure may include steps of: providing a capsule body having a space formed therein; providing an elastic body positioned between one end of the capsule body and an arm moving part and acting to move the arm moving part in a longitudinal direction toward the other end of the capsule body; providing the arm moving part movable along the longitudinal direction within the capsule body; providing an arm configured to be unfolded by longitudinal movement of the arm moving part and to move along the rail; providing an arm support part movable along the longitudinal direction within the capsule body; and providing a capsule cap configured to engage the other end of the capsule body. A rail is formed along the longitudinal direction within the capsule body. A disintegrable immediate-release formulation is positioned between the arm moving part and the arm support part, and a disintegrable sustained-release formulation is positioned between the arm support part and the capsule cap.

BRIEF DESCRIPTION OF THE DRAWINGS

FIG. 1 shows parts of a gastroretentive drug delivery device having a detachable arm structure according to one embodiment of the present disclosure.

FIG. 2 shows an assembly structure of parts of the gastroretentive drug delivery device having a detachable arm structure according to one embodiment of the present disclosure.

FIGS. 3A and 3B are views showing exemplary sizes of the gastroretentive drug delivery device having a detachable arm structure according to one embodiment of the present disclosure.

FIG. 4A is a sectional view showing the pre-operation state of the gastroretentive drug delivery device having a detachable arm structure according to an embodiment of the present disclosure.

FIG. 4B is a sectional view showing a state in which the arms of the gastroretentive drug delivery device having a detachable arm structure according to one embodiment of the present disclosure are unfolded.

FIGS. 5A to 5F are views exemplarily showing a process in which the immediate-release formulation and sustained-release formulation in the gastroretentive drug delivery device having a detachable arm structure according to one embodiment of the present disclosure are disintegrated, the arms of the device are unfolded, and the arms are finally detached.

FIGS. 6A to 6C are views exemplarily showing the structure of the gastroretentive drug delivery device having a detachable arm structure according to one embodiment of the present disclosure during operation of the drug delivery device in an arm-unfolded state and then in an arm-detached state.

FIG. 7 shows parts of a gastroretentive drug delivery device having a foldable arm structure according to one embodiment of the present disclosure.

FIGS. 8A and 8B are views showing exemplary sizes of the gastroretentive drug delivery device having a foldable arm structure according to the embodiment of the present disclosure.

FIG. 9 is a sectional view showing the pre-operation state of the gastroretentive drug delivery device having a foldable arm structure according to an embodiment of the present disclosure.

FIGS. 10A to 10D are views exemplarily showing a process in which the arms in the gastroretentive drug delivery device having a foldable arm structure according to one embodiment of the present disclosure are unfolded and folded.

FIG. 11 is a graph showing the change in the unfolded width of the arms as a function of the displacement of the elastic body in the gastroretentive drug delivery device having a detachable arm structure according to one embodiment of the present disclosure.

FIG. 12 is a graph showing the results of a dissolution test for the gastroretentive drug delivery device having a detachable arm structure in Experimental Example 2 according to one embodiment of the present disclosure.

FIG. 13 shows X-ray photographs taken after administering the gastroretentive drug delivery device having a detachable arm structure to a beagle dog in Experimental Example 5 according to one embodiment of the present disclosure.

FIG. 14 is the plasma concentration vs. time graph of rebamipide, obtained after administering the gastroretentive drug delivery device having a detachable arm structure to a beagle dog in Experimental Example 5 according to one embodiment of the present disclosure.

FIG. 15 is a graph showing the results of a dissolution test for the gastroretentive drug delivery device having a foldable arm structure in Experimental Example 7 according to one embodiment of the present disclosure.

FIG. 16 shows X-ray photographs taken after administering the gastroretentive drug delivery device having a foldable arm structure to a beagle dog in Experimental Example 8 according to one embodiment of the present disclosure.

DESCRIPTION OF SPECIFIC EMBODIMENTS

The present disclosure may be described with reference to the embodiments to be described below and the accompanying drawings. However, it is to be understood that the present disclosure is not limited to these specific embodiments and includes all changes, equivalents and substitutes included in the spirit and technical scope of the present disclosure. When describing each drawing, similar reference numerals may be used for similar components.

Terms, such as first, second, A, B or the like, may be used herein when describing various components, but these components should not be limited by the terms. The terms are used only for the purpose of distinguishing one component from other components. For example, without departing from the scope of the present disclosure, a first component may be referred to as a second component, and similarly, a second component may be referred to as a first component. The term "and/or" may be meant to include a combination of a plurality of related described items or any one of a plurality of related described items.

It is to be understood that, when one component is referred to as being "connected" or "coupled" to another component, the one component may be connected or coupled directly to another component or other components may be present between them. On the other hand, when one component is referred to as being "coupled directly" or "connected directly" to another component, it is to be understood that other components do not exist between them.

The terms used in the present application are used only to describe specific embodiments, and are not intended to limit the present disclosure. Singular expressions may include plural expressions unless clearly specified otherwise in the context thereof. In the present specification, it is to be understood that the terms "comprise", "have", etc., are intended to denote the existence of mentioned features, numbers, steps, operations, components, parts, or combinations thereof, but do not exclude the probability of existence or addition of one or more other features, numbers, steps, operations, components, parts, or combinations thereof.

Unless otherwise defined, all terms used herein, including technical and scientific terms, have the same meaning as commonly understood by those skilled in the art to which the present disclosure pertains. The terms used in general and defined in dictionaries should be interpreted as having meanings identical to those specified in the context of related technology. Unless definitely defined otherwise in the present application, the terms should not be interpreted as having ideal or excessively formative meanings.

Hereinafter, the present disclosure will be described in more detail through embodiments to be described later. The following embodiments are only to illustrate the present disclosure, and the scope of the present disclosure is not limited thereto.

FIG. 1 shows parts of a gastroretentive drug delivery device having a detachable arm structure according to one embodiment of the present disclosure. As shown in FIG. 1, a gastroretentive drug delivery device 100 may include a capsule body 1, a capsule cap 2, arms 3, arm moving part 4, an arm support part 5, and an elastic body 6. In addition, the gastroretentive drug delivery device 100 may include a disintegrable immediate-release formulation 7 and sustained-release formulation 8 for gastric retention function. The capsule body 1 may include rails 11 formed along the longitudinal direction inside the capsule body (1). In addition, the capsule body 1 may be formed to include rail-free portions 15 after the rail 11 section. The capsule body 1 may include one or more drug release windows 23 for introduction of gastric juice and release of a drug. The drug release windows 23 may be a pair of windows facing each other and may be formed in the capsule body 1. The capsule body 1 may have protrusions formed at portions that engage the capsule cap 2, and in the capsule cap 2, fitting holes may be formed, into which the protrusions may be fitted. Illustratively, the rails 11 may be formed as a pair of rails inside the capsule body 1, and the arms 3 may be a pair of arms fitted to the respective rails and may be connected to the capsule body 1. In addition, according to an embodiment, it is possible to realize a drug delivery device 100 in which more than one pair of arms (e.g., two pairs of arms (four arms)) are unfolded, and in this case, more than one corresponding pair of rails (e.g., two pairs of rails (four rails)) may be formed.

FIG. 2 shows an assembly structure of parts of the gastroretentive drug delivery device having a detachable arm structure according to one embodiment of the present disclosure. As shown in FIG. 2, the elastic body 6 may be positioned between one end of the capsule body 1 and the arm moving part 4. The elastic body 6 may be composed of materials capable of giving elastic force, such as a spring. The elastic body 6 may be mounted on the capsule body 1 in a state in which it is compressed in length. When the immediate-release formulation 7 starts to be disintegrated, the elastic body 6 may act in a direction in which the length thereof expands (that is, in a direction in which the arm moving part 4 moves toward the other end of the capsule body 1). The arm moving part 4 and the arm support part 5 are movable in the longitudinal direction within the capsule body 1, and the immediate-release formulation 7 may be disposed between the arm moving part 4 and the arm support part 5. The arms 3 may be mounted on the lateral side of the capsule body 1, and may include a rotating part 31 so that one end of each arm 3 may contact the arm moving part 4 and rotate. In addition, each arm 3 may be fitted to the rail 11 by a rotating shaft 32, and may include a groove 33 into which an extension 35 of the arm support part 5 is to be fitted so that each arm 3 is fixed in a fully folded state before it is unfolded. In addition, as will be described later, each arm 3 may include an extension 34 that may contact an extension 36 of the arm moving part 4 in a state in which each arm is perpendicularly unfolded. A sustained-release formulation 8 may be disposed between the arm support portion 5 and the capsule cap 2. The arm moving part 4, the arm support part 5, and the capsule cap 2 may include magnetic materials 41, 51 and 21, such as magnets, respectively, so as to generate mutual attraction. These magnetic materials may act to move the arm moving part 4 and the arm support part 5 in the direction of the capsule cap 2 as the immediate-release formulation and the sustained-release formulation disintegrate.

FIGS. 3A and 3B are views showing exemplary sizes of the gastroretentive drug delivery device having a detachable arm structure according to one embodiment of the present disclosure. As shown in FIG. 3A, in the pre-operation state, the gastroretentive drug delivery device 100 may have a horizontal length of 11.00 mm and a vertical length of 28.00 mm. In addition, as shown in FIG. 3B, when arms 3 are perpendicularly unfolded, the length of the gastroretentive drug delivery device 100 having the unfolded arms 3 may be 48.00 mm. However, these values are exemplary, and those skilled in the related art will be able to manufacture the gastroretentive drug delivery device 100 having appropriate dimensions, which are capable of maintaining gastric retention and allow detachment of the arms.

FIG. 4A is a sectional view showing the pre-operation state of the gastroretentive drug delivery device having a detachable arm structure according to one embodiment of the present disclosure. As shown in FIG. 4A, in the pre-operation state, the lower end of the arm moving part 4 is in contact with the rotating part 31 of each arm 3, and the rotating shaft 32 of each arm 3 is inserted into the starting part of each rail 11. In addition, the extension 35 of the arm support portion 5 is fitted into the groove 33 of each arm 3, so that it is possible to fix each arm 3 to the capsule body 1 before operation.

FIG. 4B is a sectional view showing a state in which the arms of the gastroretentive drug delivery device having a detachable arm structure according to one embodiment of the present disclosure are unfolded. As shown in FIG. 4B, when the immediate-release formulation 7 is completely disintegrated, the arm moving part 4 moves toward the other end of the capsule body 1 and comes into contact with the arm support part 5. In this process, the movement of the arm moving part 4 may allow each arm 3 to rotate with respect to the rotating shaft 32 and to be perpendicularly unfolded. As a result, the lower end of the extension 36 of the arm moving part 4 may come into contact with the rotating part 31 of each arm 3 and maintain the arms 3 in a perpendicularly unfolded state. In addition, the extension 34 of each arm 3 may come into contact with the outer surface of the extension 36 of the arm moving part 4 and maintain the arms 3 in a perpendicularly unfolded state.

FIGS. 5A to 5F are views exemplarily showing a process in which the immediate-release formulation and sustained-release formulation in the gastroretentive drug delivery device having a detachable arm structure according to one embodiment of the present disclosure are disintegrated, the arms of the device are unfolded, and the arms are finally detached.

FIG. 5A shows the pre-operation state of the gastroretentive drug delivery device 100. FIG. 5B shows that the gastroretentive drug delivery device 100 enters the stomach and the arms are unfolded while the immediate-release formulation starts to disintegrate. Specifically, when the immediate-release formulation 7 starts to disintegrate, the arm moving part 4 may move to the lower part of the capsule body 1 by the elastic body 6. This movement of the arm moving part 4 may apply a force to the rotating part 31 of each arm 3, whereby the arms 3 may be unfolded while rotating about the rotating shaft 32. FIG. 5C shows the gastroretentive drug delivery device 100 in which the immediate-release formulation 7 is completely disintegrated and the arms 3 are perpendicularly unfolded. As described above, when the immediate-release formulation 7 is completely disintegrated, the arm moving part 4 may reach the arm support part 5, and the arms 3 may be perpendicularly unfolded to exhibit gastric retention ability.

FIG. 5D shows that the unfolded arms 3 moves to the lower part of the capsule body 1 while the sustained-formulation 8 is disintegrated. As described above, after the arms 3 are perpendicularly unfolded, the extension 36 of the arm moving part 4 and the extension 34 of each arm 3 may contribute to maintaining the arms 3 in the perpendicularly unfolded state. As the sustained-release formulation 8 is disintegrated, the arm support part 5 combined with the arm moving part 4 may move to the lower part the capsule body 1 by the magnetic force between the arm support part 5 and the capsule cap 2. At this time, the perpendicularly unfolded arms 3 combined with the arm moving part 4 may move to the lower part of the capsule body 1 along the rails 11 while maintaining the perpendicularly unfolded state.

FIG. 5E shows a state in which the sustained-release formulation 8 has been completely disintegrated and the arms 3 have moved to the end of the section of each rail 11. FIG. 5F shows a state in which the arms 3 are detached from the capsule body 1. When each arm 3 comes down to the rail-free portion 15, the arms 3 are detached from the capsule body 1 while leaving the rails. As a result, the capsule body 1 and the detached arms 3 lose the gastric retention function, and thus may be discharged to the outside of the body. In addition, the length of each rail 11 of the gastroretentive drug delivery device 100 may be changed so that the time taken for the arms 3 to be detached may be adjusted. For example, by making the length of the rail 11 shorter than a predetermined length, it is possible to produce the gastroretentive drug delivery device 100 in which the time taken for the arms 3 to be detached is shorter. In this case, the arms 3 of the drug delivery device 100 may be detached before complete disintegration of the sustained-release formulation 8 and may move to the small intestine at an earlier time, whereby the degree to which the drug is released in the stomach and intestines may be controlled.

FIGS. 6A to 6C are views exemplarily showing the structure of the gastroretentive drug delivery device having a detachable arm structure according to one embodiment of the present disclosure during operation of the drug delivery device in an arm-unfolded state and then in an arm-detached state.

FIG. 6A is a detailed perspective view of FIG. 5D. As shown in FIG. 6A, the perpendicularly unfolded arms 3 may move along the rails 11. FIG. 6B is a detailed perspective view of FIG. 5E. As shown in FIG. 6B, the arms 3 have reached the rail-free portions 15, and the rotating part 31 and the rail 11 are uncoupled from each other. FIG. 6C is a detailed perspective view of FIG. 5F. As shown in FIG. 6C, the uncoupled arms 3 detach from the capsule body 1.

FIG. 7 shows parts of a gastroretentive drug delivery device having a foldable arm structure according to one embodiment of the present disclosure. As shown in FIG. 7, a gastroretentive drug delivery device 200 having a foldable arm structure may include a capsule body 9, a capsule cap 10, an arm 112, and an elastic body 16. In addition, for gastric retention function, a disintegrable immediate-release formulation 13, sustained-release formulation 14 and sustained-release supporter 17 may be included in the gastroretentive drug delivery device 200. The immediate-release formulation 13 may be prepared to be disintegrated quickly so that gastric retention function is quickly initiated by quickly unfolding the arms. The capsule body 9 may include one or more drug release windows 93 for introduction of gastric juice and release of a drug. The drug release windows 93 may be a pair of windows facing each other, and may be formed in the capsule body 9. The capsule body 9 may have fitting holes 120 formed at portions which engage the capsule cap 10, and in the capsule cap 10, protrusions 121 that may be fitted into the fitting holes 120 may be formed.

The arm 112 may include a first hinge part 114, a second hinge part 115, a third hinge part 116, and an elastic support part 111, which enable unfolding and folding. The arm 112 may be mounted at one end of the capsule body 9. Illustratively, as shown in FIG. 7, the connection portion between the third hinge parts 116 may be formed so that the protrusion 150 in the capsule body 9 may fit into the connection portion. The first hinge part 114 may engage the elastic support part 111. The second hinge part 115 may engage a wing 140 of the arm 112, and may be connected rotatably to the first hinge part 114. The third hinge part 116 may be positioned at one end of each wing 140, and may be connected rotatably to the second hinge part 115. The sustained-release supporter 17 may be positioned to face the third hinge part 116, and the immediate-release formulation 13 may be positioned to face the elastic support part 111, and the sustained-release formulation 14 may be positioned between the sustained-release supporter 17 and the immediate-release formulation 13. As shown in FIG. 9 to be described later, the immediate-release formulation 13 may be positioned in an area defined by the first hinge part 114, the second hinge part 115 and the elastic support part 111, and thus the diameter of the immediate-release formulation 13 may be smaller than the diameter of each of the sustained-release formulation 14 and the sustained-release supporter 17. In addition, as illustrated in FIG. 7, the arm 112 may have a pair of wings 140. In this case, to enable the unfolding and folding of the pair of wings 140, the arm 112 may have a pair of first hinge parts 114, a pair of second hinge parts 115 and a pair of third hinge parts 116. Furthermore, according to an embodiment, more than one arm 112 having a pair of wings may also be embodied, and in this case, each arm 112 may be embodied to have a pair of first hinge parts, a pair of second hinge parts and a pair of third hinge parts.

In addition, as shown in FIG. 7, the elastic body 16 may be positioned between the arm 112 and the capsule cap 10. The elastic body 16 may be composed of materials capable of providing an elastic force, such as a spring. The elastic body 16 may be mounted on the capsule body 9 in a state in which it is compressed in length. When the immediate-release formulation 13 (and subsequently the sustained-release formulation 14 and the sustained-release supporter 17) starts to be disintegrated, the elastic body 16 may act in a direction in which the length thereof expands (that is, in a direction in which the elastic support part 111 moves toward the one end of the capsule body 9. The elastic support part 111 may include an extension 130 extending toward the other end of the capsule body 9. The extension 130 may be inserted into the inner space of the elastic body 16, and may function to guide the elastic force of the elastic body 16 toward one end of the capsule body 9.

FIGS. 8A and 8B are views showing exemplary sizes of the gastroretentive drug delivery device having a foldable arm structure according to the embodiment of the present disclosure. As shown in FIG. 8A, in the pre-operation state, the height of the gastroretentive drug delivery device 200 may be 9.8 mm, and the lengthwise length thereof may be 27.00 mm. In addition, as shown in FIG. 8B, when the arm 112 is unfolded, the unfolding length between the two wings 140 may be 33.00 mm. However, these values are exemplary, and those of ordinary skill in the related art will be able to produce the gastroretentive drug delivery device 200 having appropriate dimensions, which are capable of maintaining and terminating gastric retention.

FIG. 9 is a sectional view showing the pre-operation state of the gastroretentive drug delivery device having a foldable arm structure according to an embodiment of the present disclosure. As described above, in the pre-operation state, the immediate-release formulation 13 may be disposed in an area defined by the elastic support part 111, the first hinge part 114 and the second hinge part 115. The sustained-release formulation 14 and the sustained-release supporter 17 may be disposed following the immediate-release formulation 13 in the capsule body 9 toward one end of the capsule body 9. As will be described later, the gastroretentive drug delivery device 200 may perform gastric retention function and detachment function as the elastic support part 111 moves while the immediate-release formulation 13, the sustained-release formulation 14 and the sustained-release supporter 17 are sequentially disintegrated.

FIGS. 10A to 10D are views exemplarily showing a process in which the arms in the gastroretentive drug delivery device having a foldable arm structure according to one embodiment of the present disclosure are unfolded and folded.

FIG. 10A is a view showing the arm 112 and surrounding components in the pre-operation state. FIG. 10B is a view showing a state in which the arms 112 are unfolded while the immediate-release formulation 13 is disintegrated. As shown in FIG. 10B, the elastic support part 111 moves toward one end of the capsule body 9 by the elastic force as the immediate-release formulation 13 is disintegrated. This movement of the elastic support part 111 may rotate the first hinge part 114, the second hinge part 115 and the third hinge part 116 in the direction in which the wings 140 of the arm 112 are unfolded. As a result, a gastric retention function may be achieved by unfolding of the wings 140 of the arm 112.

FIG. 10C is a view showing that the arm 112 are maintained in an unfolded state as the sustained-release formulation 14 is disintegrated. As shown in FIG. 10C, the elastic support part 111 moves toward one end of the capsule body 9 by the elastic force as the sustained-release formulation 14 is slowly disintegrated. This movement of the elastic support part 111 may further rotate the first hinge part 114, the second hinge part 115 and the third hinge part 116. During the rotational movement of the hinge parts by the disintegration of the sustained-release formulation 14, the unfolded length of the wings 140 of the arm 112 is maintained at a predetermined length or more. The predetermined length may be set to a minimum value at which the gastric retention function may be maintained, and is a value that may be derived through an experiment in the relevant technical field.

FIG. 10D is a view showing a state in which the arms 112 are folded again as the sustained-release supporter 17 is disintegrated. As shown in FIG. 10D, the elastic support part 111 moves toward one end of the capsule body 9 by the elastic force as the sustained-release supporter 17 is disintegrated. This movement of the elastic support part 111 may further rotate the first hinge part 114, the second hinge part 115 and the third hinge part 116 in the direction in which the wings 140 of the arm 112 are folded. When the sustained-release supporter 17 is completely disintegrated and the wings 140 of the arm 112 are folded, the capsule body 9 loses the gastric retention function and may be discharged out of the body.

FIG. 11 is a graph showing the change in the unfolded width of the arm 112 (i.e., the unfolded length of the wings 140) as a function of the displacement of the elastic body 16 in the gastroretentive drug delivery device 200 having a foldable arm structure according to one embodiment of the present disclosure. As illustrated in FIGS. 8A and 8B, when the immediate-release formulation 13 in the produced drug delivery device 200 is rapidly disintegrated, the length of the elastic body 16 may expand by 5 mm. The width of the arm 112 unfolded by this expansion of the elastic body 16 may be 30 mm or more, and thus gastric retention function may be obtained. While the sustained-release formulation 14 containing a pharmacologically active drug releases the drug, the length of the elastic body 16 may expand from 5 mm to 7.5 mm, and the unfolded width of the arm 112 may be maintained at 30 mm or more, for example, up to 33.1 mm. Then, as the sustained-release supporter 17 is disintegrated, the length of the elastic body 16 expands from 7.5 mm to 10 mm, the arm 112 is folded by the rotating hinge structures 114, 115 and 116, and the device 200 loses gastric retention function.

The present disclosure may provide a method for manufacturing a gastroretentive drug delivery device, the method including steps of: preparing a capsule device including a capsule body and internal constituent components; preparing an immediate-release portion and sustained-release portion containing a pharmacologically active drug; and assembling the capsule device.

The capsule device of the present disclosure may be composed of materials selected from the group consisting of a biodegradable synthetic polymer, a natural polymer, a synthetic resin for oral administration, and mixtures thereof. The biodegradable synthetic polymer may be spontaneously and slowly degraded after a certain period of time, and may include a polymer having one or more characteristics selected from among biocompatibility, blood compatibility, anticalcification properties, and ability to form cellular nutrient components and intercellular matrix. This biodegradable polymer may be selected from, but not limited to, fibrin, collagen, gelatin, chitosan, alginate, hyaluronic acid, dextran, poly(lactic acid), poly(glycolic acid) (PGA), poly(lactic-co-glycolic acid) (PLGA), poly-ε-(caprolactone), polyanhydride, polyorthoester, polyvinyl alcohol, polyethylene glycol, polyurethane, polyacrylic acid, poly-N-isopropylacrylamide, a poly(ethylene oxide)-poly(propylene oxide)-poly(ethylene oxide) copolymer, copolymers thereof, or mixtures thereof. In addition, conventionally used materials, such as synthetic resins and natural polymers for oral administration, may also be used as materials for the gastroretentive drug delivery device without particular limitation. These materials for the gastroretentive capsule device may remain in the stomach for a long period of time without dissolving, and then may lose gastric retention function and may be discharged out of the body after the drug contained in the sustained-release portion is completely released.

The capsule device of the present disclosure may be produced by a conventionally known molding method, or may be designed and mass-produced using a 3D printer.

According to the present disclosure, the pharmaceutical composition containing the pharmacologically active drug is slowly released while the gastroretentive drug delivery device remains in the stomach. This pharmacologically active drug may be released into the body through the drug release windows positioned in the capsule body. The drug release windows provide paths through which gastric juice and the pharmacologically active drug are introduced/released, and may have various shapes, sizes and numbers so that the dissolution profile of the drug may be adjusted.

According to the present disclosure, the drug release windows may have various shapes, such as a circular or polygonal shape, various sizes (e.g., nano-size, micro-size, etc.), and various numbers. The drug release windows of the present disclosure may exist in the form of drug release holes or windows connecting the inside and the outside of the capsule body. These drug release holes or windows may be randomly arranged in the capsule body or may exist in plural in the form of a pair of windows facing each other. When one or more pairs of windows are positioned to face each other, the dissolution profile of the drug may be adjusted by improving the rates of introduction and release of gastric juice and the pharmacologically active drug.

In the present disclosure, the process of obtaining the immediate-release portion may include steps of: 1) mixing a pharmacologically active drug, a disintegrant and a binder; 2) preparing a binding solution by mixing ethanol and distilled water; 3) granulating the mixture resulting from steps 1) and 2); and 4) sieving the prepared granules, followed by mixing with a lubricant and compression into a tablet, thereby obtaining an immediate-release tablet.

The immediate-release portion may be disintegrated and dissolved by gastric juice, so that the arms may be expanded quickly and initiate gastric retention function. At the same time, the immediate-release portion may release the pharmacologically active drug, thereby enabling the drug to reach the effective blood concentration in the initial stage.

According to one embodiment of the present disclosure, the disintegrant may be used to promote initial disintegration of the formulation and dissolution of the pharmacologically active component by absorbing water. The disintegrant may be selected from, but not limited to, polyvinylpolydone, sodium starch glycolate, crospovidone, low-substituted hydroxypropyl cellulose, calcium carboxymethylcellulose, and the like. Excipients may include, but not limited to, sweeteners, binders, solubilizers, solubilizing aids, wetting agents, emulsifiers, isotonic agents, adsorbents, disintegrants, antioxidants, preservatives, lubricants, fillers, fragrances, etc. Examples of the excipients include, but not limited to, lactose, dextrose, sucrose, mannitol, sorbitol, cellulose, glycine, silica, magnesium aluminum silicate, starch, gelatin, tragacanth rubber, arginic acid, sodium alginate, methylcellulose, sodium carboxylmethylcellulose, water, ethanol, polyethylene glycol, polyvinylpyrrolidone, sodium chloride, calcium chloride, orange essence, strawberry essence, vanilla flavor, and the like. Lubricants may include, but not limited to, cellulose, calcium silicate, corn starch, lactose, sucrose, dextrose, calcium phosphate, stearic acid, magnesium stearate, calcium stearate, gelatin, talc, and the like.

A pharmacologically active drug that may be used in the present disclosure may be released into the body through the drug release window included in the capsule body of the gastroretentive drug delivery device. This pharmacologically active drug may be in the form of various pharmaceutically acceptable formulations and may be included inside the capsule body. For example, as the pharmacologically active drug that is used in the present disclosure, there may be a drug that is specifically absorbed mainly in the stomach or upper small intestine, a drug that is locally absorbed in the stomach, a drug that is unstable or has a low absorption rate in the lower stomach, a drug that has a low absorption rate in the small intestine and large intestine, or a drug that has high dissolution rate and absorption rate in an acidic environment. This pharmacologically active drug may be, for example, riboflavin, acyclovir, rebamipide, furosemide, levodopa, albuterol, 5-fluorouracil, an antacid, captopril, diazepam, diltiazem, propranolol, and or like. Any drug having a good absorption rate mainly in the stomach may be used as the pharmacologically active drug.

The pharmaceutical composition of the present disclosure may further contain conventional non-toxic pharmaceutically acceptable additives in addition to the above-described pharmacologically active drug. For example, the pharmaceutical composition of the present disclosure may contain at least one selected from the group consisting of carriers, adjuvants and excipients, and may be prepared according to a conventional method. If necessary, the pharmaceutical composition may be prepared as various formulations, such as powder, beads, granules, pellets, capsules, or tablets. The form of the formulation may be changed depending on the desired dissolution profile of the drug.

The pharmaceutical composition of the present disclosure may further contain one or more components selected from the group consisting of excipients, binders, disintegrants, lubricants, solubilizers, solubilizing aids, wetting agents, emulsifiers, isotonic agents, adsorbents, disintegrants, antioxidants, preservatives, lubricants, fillers, and mixtures thereof.

The process of obtaining the sustained-release portion in the present disclosure may include steps of: 1) mixing a pharmacologically active drug, a sustainedly releasing agent and an excipient; 2) preparing a binding solution by mixing ethanol and distilled water; 3) granulating the mixture resulting from steps 1) and 2); and 4) sieving the prepared granules, followed by mixing with a lubricant and compression into a tablet, thereby obtaining a sustained-release tablet.

In the present disclosure, the pharmaceutical composition containing the pharmacologically active drug may be a sustained-release formulation, and the release rate of the pharmacologically active drug from the sustained-release formulation may be adjusted depending on the type and ratio of the sustainedly releasing agent added.

The sustainedly releasing agent may absorb media such as bodily fluids and gastric juice, so that particles may change into a gel phase by entanglement and binding, thereby controlling rapid release of the drug. In addition, the sustainedly releasing agent may control release of the drug by being slowly eroded by gastric juice.

The type of excipient contained in the sustained-release portion may be the same as the type of excipient contained in the immediate-release portion. In addition, the type of lubricant contained in the sustained-release portion may be the same as the type of lubricant contained in the immediate-release portion.

Examples 1 to 5: Production of Gastroretentive Drug Delivery Devices Having Detachable Arm Structure Step 1) Production of Gastroretentive Drug Delivery Capsule Having Detachable Arm Structure According to these Examples, the design of the gastroretentive drug delivery capsule may be completed using the Rhino 6® (Robert McNeel & Associates, WA, USA) computer-aided design (CAD) program. In addition, components constituting the capsule may be produced using the Mii Craft U50 (Mii Craft, PO, UAE) digital light processing (DLP) type 3D printer and a photocurable resin.

The time that the arms of the gastroretentive drug delivery capsule are retained may be determined according to the length of the rail 11 of the body. Accordingly, gastroretentive capsules were produced depending on the rail length, and exemplary production examples are shown in Table 1 below.

TABLE 1

|  | Production Example 1-1 | Production Example 1-2 | Production Example 1-3 |
|---|---|---|---|
| Length (mm) of rail 11 | 16.75 | 15.75 | 14.75 |

Step 2) Production of Immediate-Release Tablet

According to these Examples, 100 mg of rebamipide was homogeneously mixed with Kollicoat®, microcrystalline cellulose, low-substituted hydroxypropyl cellulose, and crospovidone. Separately, a binding solution was prepared by adding 3 mL of distilled water to 7 mL of ethanol, and the binding solution was added to the mixture. The resulting mixture was sieved through a 20-mesh sieve and then dried at 60° C. for 60 minutes. The dried mixture was sieved through a 20-mesh sieve, and 1.9 mg of stearic acid was added, followed by homogeneous mixing, thereby preparing granules. Table 2 below shows the content of each component in the granules prepared according to each of exemplary Production Examples 2-1, 2-2 and 2-3. The prepared granules were compressed into tablets under a pressure of 0.5 tons, thereby producing rebamipide immediate-release tablets.

TABLE 2

| Component | | Production Example 2-1 | | Production Example 2-2 | | Production Example 2-3 | |
|---|---|---|---|---|---|---|---|
| | | Amount used (mg/T) | Weight (%) | Amount used (mg/T) | Weight (%) | Amount used (mg/T) | Weight (%) |
| Pharmacologically active drug | Rebamipide | 100 | 52.6 | 100 | 52.6 | 100 | 52.6 |
| Excipient | Microcrystalline cellulose | 6.4 | 3.4 | 58.1 | 30.6 | — | — |
| Disintegrant | Low-substituted hydroxypropyl cellulose | 76 | 40 | | | 88.1 | 46.4 |
| | Crospovidone | — | — | 15 | 7.9 | — | — |
| Binder | Kollicoat | 5.7 | 3 | 15 | 7.9 | — | — |
| Lubricant | Magnesium stearate (%) | 1.9 | 1 | 1.9 | 1 | 1.9 | 1 |
| | Total mass | 190 | 100 | 190 | 100 | 190 | 100 |

Step 3) Production of Sustained-Release Tablet

According to this Example, 200 mg of rebamipide was homogeneously mixed with microcrystalline cellulose, hydroxy propyl methyl cellulose (HPMC) 2208-100 cps, and HPMC 2208-4000 cps. Separately, a binding solution was prepared by 3 mL of distilled water to 7 mL of ethanol, and the binding solution was added to the mixture. The resulting mixture was sieved through a 20-mesh sieve and then dried at 60° C. for 60 minutes. The dried mixture was sieved through a 20-mesh sieve, and 3 mg of stearic acid was added thereto, followed by homogeneous mixing, thereby preparing granules. Table 3 below shows the content of each component in the granules prepared according to each of exemplary Production Examples 3-1, 3-2 and 3-3. The prepared granules were compressed into tablets under a pressure of 1 ton, thereby producing rebamipide sustained-release tablets.

TABLE 3

| Component | | Production Example 3-1 | | Production Example 3-2 | | Production Example 3-3 | |
|---|---|---|---|---|---|---|---|
| | | Amount used (mg/T) | Weight (%) | Amount used (mg/T) | Weight (%) | Amount used (mg/T) | Weight (%) |
| Pharmacologically active drug | Rebamipide | 200 | 66.7 | 200 | 66.7 | 200 | 66.7 |
| Excipient | Microcrystalline cellulose | 67 | 22.3 | 15 | 5 | 15 | 5 |
| Sustainedly releasing agent | HPMC2208-100 cps | 30 | 10 | 73 | 24.3 | 67 | 22.3 |
| | HPMC2208-4000 cps | — | — | 9 | 3 | 15 | 5 |
| Lubricant | Magnesium stearate (%) | 3 | 1 | 3 | 1 | 3 | 1 |
| | Total mass | 300 | 100 | 300 | 100 | 300 | 100 |

Step 4) Production of Gastroretentive Drug Delivery Device Having Detachable Arm Structure According to this Example, a gastroretentive drug delivery device having a detachable arm structure may be produced by combining the gastroretentive capsule of Production example 1-1 produced in Step 1, the immediate-release tablet of Production Example 2-3 produced in Step 2, and the sustained-release tablet (each of Production Examples 3-1 to 3-3) produced in Step 3 (Examples 1 to 3).

In addition, a gastroretentive drug delivery device having a detachable arm structure may be produced by combining the gastroretentive capsule (each of Production Examples 1-2 and 1-3) produced in Step 1, the immediate-release tablet of Production Example 2-3 produced in Step 2, and the sustained-release tablet of Production Example 3-3 produced in Step 3 (Examples 4 and 5). The production configurations of these exemplary Examples are shown in Table 4 below.

TABLE 4

|  | Example 1 | Example 2 | Example 3 | Example 4 | Example 5 |
|---|---|---|---|---|---|
| Gastroretentive capsule | Production Example 1-1 | Production Example 1-1 | Production Example 1-1 | Production Example 1-2 | Production Example 1-3 |
| Immediate-release tablet | Production Example 2-3 | Production Example 2-3 | Production Example 2-3 | Production Example 2-3 | Production Example 2-3 |
| Sustained-release tablet | Production Example 3-1 | Production Example 3-2 | Production Example 3-3 | Production Example 3-3 | Production Example 3-3 |

Examples 6 to 8: Production of Gastroretentive Drug Delivery Devices Having Foldable Arm Structure Step 1) Production of Gastroretentive Drug Delivery Capsule Having Foldable Arm Structure According to these Examples, the design of the gastroretentive drug delivery capsule may be completed using the Rhino 6® (Robert McNeel & Associates, WA, USA) computer-aided design (CAD) program. In addition, components constituting the capsule may be produced using the fused deposition modeling (FDM)-type Raise3D N2 model 3D printer and PLA (poly(lactic acid)) resin (Production Example 4).

Step 2) Production of Immediate-Release Tablet

According to this Example, lactose (Flow-lac 100) and magnesium stearate may be homogeneously mixed together at a ratio of 99.5:0.5. Using a hydraulic tablet press (manufactured by Carver, Inc., for example) and a circular punch having a diameter of 5 mm, the prepared mixture may be compressed into tablets under a pressure of 0.3 tons, thereby producing circular immediate-release initiation tablets, each having a diameter of 5 mm and a height of 5 mm. An exemplary production example (Production Example 5) of the immediate-release tablet is shown in Table 5 below.

TABLE 5

|  |  | Production Example 5 | |
|---|---|---|---|
| Production method | | Amount used (mg/T) | Weight (%) |
| Excipient | Flow-lac 100 | 124.375 | 99.5 |
| Lubricant | Magnesium stearate | 0.625 | 0.5 |
| Total mass (mg) | | 125 | |
| Tablet compression pressure (ton) | | 0.3 | |

Step 3) Production of Riboflavin Sustained-Release Tablet

According to these Examples, riboflavin may be homogeneously mixed with lactose (Flow-lac 100), hydroxy propyl methyl cellulose (Metolose 90SH-4000SR) and magnesium stearate at various ratios. The prepared mixture was compressed into tablet using a manual single punch tablet press (e.g., KTP-05 manufactured by Koreamedi Co. Ltd.) and a circular punch having a diameter of 8 mm, thereby producing riboflavin sustained-release tablets, each having a diameter of 8 mm and a height of 2.5 mm. Exemplary production examples (Production Examples 6-1 to 6-3) of the sustained-release tablet are shown in Table 6 below.

TABLE 6

| | | Production Example 6-1 | | Production Example 6-2 | | ProductionEexample 6-3 | |
|---|---|---|---|---|---|---|---|
| Production method | | Amount used (mg/T) | Weight (%) | Amount used (mg/T) | Weight (%) | Amount used (mg/T) | Weight (%) |
| Pharmacologically active drug | Riboflavin | 20 | 13.3 | 20 | 13.3 | 20 | 13.3 |
| Excipient | Flow-lac 100 | 117.25 | 78.2 | 108.25 | 72.2 | 103.25 | 68.8 |
| Sustainedly releasing agent | Metolose 90SH-4000SR | 12 | 8 | 21 | 14 | 26 | 17.3 |
| Lubricant | Magnesium stearate (%) | 0.75 | 0.5 | 0.75 | 0.5 | 0.75 | 0.5 |
| Total mass (mg) | | 150 | | 150 | | 150 | |

Step 4) Production of Sustained-Release Support Tablet

According to this Example, lactose (Flow-lac 100), hydroxy propyl methyl cellulose (Metolose 90SH-15000SR) and magnesium stearate may be homogeneously mixed together at various ratios. Using a manual single punch tablet press (e.g., KTP-05 manufactured by Koreamedi Co. Ltd.) and a circular punch having a diameter of 8 mm, the prepared mixture was compressed into tablets, thereby producing sustained-release support tablets, each having a diameter of 8 mm and a height of 2.5 mm. Exemplary production examples (Production Examples 7-1 to 7-3) of the sustained-release support tablet are shown in Table 7 below.

TABLE 7

|  |  | Production Example 7-1 | | Production Example 7-2 | | Production Example 7-3 | |
| --- | --- | --- | --- | --- | --- | --- | --- |
|  | Production method | Amount used (mg/T) | Weight (%) | Amount used (mg/T) | Weight (%) | Amount used (mg/T) | Weight (%) |
| Excipient | Flow-lac 100 | 139.25 | 92.8 | 128.25 | 85.5 | 99.25 | 66.2 |
| Sustainedly releasing agent | Metolose 90SH-15000SR | 10 | 6.7 | 21 | 14 | 50 | 33.3 |
| Lubricant | Magnesium stearate (%) | 0.75 | 0.5 | 0.75 | 0.5 | 0.75 | 0.5 |
| Total mass (mg) |  | 150 | | 150 | | 150 | |

Step 5) Production of Gastroretentive Drug Delivery Device Having Folded Arm Structure A gastroretentive drug delivery device having a foldable arm structure may be produced by combining the gastroretentive capsule of Production Example 4 of Step 1, the immediate-release tablet of Production Example 5 of Step 2, the riboflavin sustained-release tablet of Production Example 6-1 of Step 3, and the sustained-release support tablet of Production Example 7-1 of Step 4 (Example 6). A gastroretentive drug delivery device having a foldable arm structure may be produced by combining the gastroretentive capsule of Production Example 4 of Step 1, the immediate-release tablet of Production Example 5 of Step 2, the riboflavin sustained-release tablet of Production Example 6-2 of Step 3, and the sustained-release support tablet of Production Example 7-2 of Step 4 (Example 7). In addition, a gastroretentive drug delivery device having a foldable arm structure may be produced by combining the gastroretentive capsule of Production Example 4 of Step 1, the immediate-release tablet of Production Example 5 of Step 2, the riboflavin sustained-release tablet of Production Example 6-3 of Step 3, and the sustained-release support tablet of Production Example 7-3 of Step 4 (Example 8). The production configurations of these exemplary examples are shown in Table 8 below.

TABLE 8

| Assembly configuration | Example 6 | Example 7 | Example 8 |
| --- | --- | --- | --- |
| Gastroretentive drug delivery capsule | Production Example 4 | Production Example 4 | Production Example 4 |
| Sustained-release initiating tablet (operator) | Production Example 5 | Production Example 5 | Production Example 5 |
| Riboflavin sustained-release tablet | Production Example 6-1 | Production Example 6-2 | Production Example 6-3 |
| Sustained-release support tablet (supporter) | Production Example 7-1 | Production Example 7-2 | Production Example 7-3 |

Experimental Example 1: Experiment on Operation of Gastroretentive Drug Delivery Capsule Having Detachable Arm Structure For each combination of the gastroretentive drug delivery capsule produced in Production Example 1 and the immediate-release tablets produced in Production Examples 2-1 to 2-3, the time taken for the arm to be unfolded was evaluated. The results of the evaluation are shown in Table 9 below.

TABLE 9

|  | Configuration 1 | Configuration 2 | Configuration 3 |
| --- | --- | --- | --- |
| Drug delivery capsule | Production Example 1-1 | Production Example 1-1 | Production Example 1-1 |
| Inserted sustained-release tablet | Production Example 2-1 | Production Example 2-2 | Production Example 2-3 |
| Release area | Drug release window 13 | Drug release window 13 | Drug release window 13 |
| Time taken for arm to be unfolded | 10 min | 8 min | Within 30 sec |

Experimental Example 2: Dissolution Test for Immediate-Release Portion

To evaluate the dissolution time of the immediate-release portion, a dissolution test for the immediate-release tablet produced in Production Example 2-3 and configuration 3 of Table 9 above was performed. This dissolution test was performed according to dissolution test method II of the general test method described in the Korean Pharmacopoeia. The results of the dissolution test are shown in Table 10 below.

TABLE 10

|  | Dissolution rate (%) | |
| --- | --- | --- |
| Dissolution time | Production Example 2-3 | Configuration 3 |
| 0.25 min | 10.74 | 12.71 |
| 0.5 min | 81.86 | 59.01 |
| 0.75 min | 99.84 | 83.17 |
| 1 min | 102.74 | 88.95 |
| 1.5 min | 101.46 | 90.20 |
| 2 min | 98.67 | 91.62 |
| 2.5 min | 100.21 | 94.29 |
| 3 min | 101.07 | 95.10 |
| 5 min | 100.63 | 96.01 |

As shown in Table 10 above, 80% or more of the drug in each of the immediate-release tablet of Production Example 2-3 and configuration 3 was dissolved within 1 minute. Thereby, it could be confirmed that there is no abnormality in quick unfolding of the arm of the gastroretentive drug delivery device. The results in Table 10 above are shown in FIG. 12.

Experimental Example 3: Maintenance Time of Arm of Drug Delivery Device Depending on Excipient Composition of Sustained-Release Tablet An experiment was performed to examine the maintenance time of the arm depending on the excipient composition of the sustained-release tablet in the gastroretentive drug delivery device having a detachable arm structure, produced in each of Examples 1 to 3. For this evaluation, a dissolution test was performed according to dissolution test method II of the general test method described in the Korean Pharmacopoeia. The results of the dissolution test are shown in Table 11 below.

TABLE 11

|  | Example 1 | Example 2 | Example 3 |
| --- | --- | --- | --- |
| Drug delivery capsule | Production Example 1-1 | Production Example 1-1 | Production Example 1-1 |
| Inserted immediate-release portion | Production Example 2-3 | Production Example 2-3 | Production Example 2-3 |
| Inserted sustained-release portion | Production Example 3-1 | Production Example 3-2 | Production Example 3-3 |
| Release area | Drug release window 13 | Drug release window 13 | Drug release window 13 |
| Time during which arm is maintained | 12.3 hours | 18 hours | 22.5 hours |

From the results in Table 11 above, it could be confirmed that the time during which the arm is maintained was determined depending on the change in the composition of the sustained-release portion. This means that the sustained-release property of the drug delivery device can be adjusted to 12 to 24 hours or more depending on the purpose of administration.

Experimental Example 4: Maintenance Time of Arm Depending on Rail Length of Drug Delivery Device An experiment was performed to examine the maintenance time of the arm depending on the rail length in the gastroretentive drug delivery device having a detachable arm structure, produced in each of Examples 3 to 5. This experiment is an experiment for examining whether gastric retention can be maintained and controlled depending on the change in the structure of the drug delivery device itself regardless of the composition of the tablet. For this evaluation, a dissolution test was performed according to dissolution test method II of the general test method described in the Korean Pharmacopoeia. The results of the dissolution test are shown in Table 12 below.

TABLE 12

|  | Example 3 | Example 4 | Example 5 |
| --- | --- | --- | --- |
| Drug delivery capsule | Production Example 1-1 | Production Example 1-1 | Production Example 1-1 |
| Inserted immediate-release portion | Production Example 2-3 | Production Example 2-3 | Production Example 2-3 |
| Inserted sustained-release portion | Production Example 3-3 | Production Example 3-3 | Production Example 3-3 |
| Length (mm) of rail 11 | 16.75 | 15.75 | 14.75 |
| Time during which arm is maintained | 22.5 hours | 18 hours | 13.7 hours |

From the results in Table 12 above, it was confirmed that the maintenance time of the arm was determined according to the change in the rail length of the capsule body. This suggests that the drug delivery device itself can maintain and control gastric retention regardless of the sustained-release property of the tablet.

Experimental Example 5: Evaluation of Gastric Retention Ability and Pharmacodynamics of Gastroretentive Drug Delivery Device Having Detachable Arm Structure In this experiment, the gastroretentive drug delivery device having a detachable arm structure, produced in Example 3, and a commercially available rebamipide tablet of a Comparative Example, were administered to beagle dogs. In this experiment, whether the gastric retention ability and bioavailability of the gastroretentive drug delivery device were improved was examined by taking X-ray photographs with time and analyzing the plasma concentration of the drug. The results of this experiment are shown in Table 13 below and FIG. 14.

(1) Experimental Animals

Six male beagle dogs (aged about 14 to 15 months; Covance Beagles, Orient Bio Jeongeup Center, Korea) were housed in stainless steel mesh breeding cages (895 mm (W)×795 mm (L)×765 mm (H)) at a density of one animal per cage during quarantine, acclimatization, administration and observation periods. For use in the experiment, animals were selected based on feed intake and body weight and divided into two groups (each consisting of three animals) so that the average weight was as equal as possible between the two groups. The experiment was conducted in Room No. 2 of the first animal breeding zone of Knotus Co., Ltd. under the following conditions: temperature: 23±3° C.; relative humidity: 55±15%; ventilation frequency: 10 or more times/hour; lighting time: 12 hours (lighting up at 8 am and turning off at 8 pm); and illumination density: 150-300 Lux. The animals used in the experiment were fasted for 12 hours or more before drug administration.

(2) Experimental Method

To group 1, the commercially available rebamipide of a Comparative Example was orally administered at 8 hour-intervals. To group 2, the gastroretentive drug delivery device having a detachable arm structure, produced in Example 3, was orally administered once. For group 1, before administration and at 0.25, 0.5, 0.75, 1, 1.5, 2, 3, 4, 6, 8, 8.25, 8.5, 8.75, 9, 9.5, 10, 11, 12, 14, 16, 16.25, 16.5, 16.75, 17, 17.5, 18, 19, 20, 22 and 24 hours after administration (a total of 31 time points), a blood sample was taken and the plasma concentration of rebamipide was quantified. For group 2, before administration and at 0.25, 0.5, 1, 1.5, 2, 2.5, 3, 4, 5, 6, 8, 10, 12, 16, 19, 22, 24, 28, 32 and 36 hours after administration (a total of 21 time points), a blood sample was taken and the plasma concentration of rebamipide was quantified. X-ray photography was performed only in group 2 at 0, 0.167, 1, 3, 6, 8, 12, 16, 19, 22, 24, 28, 32, 36 and 48 hours. Among the taken photographs, photographs taken at 0, 1, 24 and 36 hours are shown in FIG. 13.

TABLE 13

| Formulation | <Comparative Example> | <Example 3> |
| --- | --- | --- |
| $t_{1/2}$ (h) | 1.95 | 9.95 |
| $C_{max}$ (ng/mL) | 538.5 | 539.69 |
| $AUC_{0\text{-}24\,h}$ (ng · h/mL) | 3855 | 8085 |
| Relative bioavailability (%) | 100 | 209.7 |

As shown in Table 13 above, it was confirmed that, when Example 3 was administered to the beagle dogs, the drug half-life ($t_{1/2}$) was 9.95 hours, which was about 5 times longer than that of the group to which the Comparative Example was administered ($t_{1/2}$=1.95 hours), and the plasma concentration of the drug was stably maintained (FIG. 14).

When comparing the area under the blood concentration-time curve (AUC) between the two groups, it was confirmed that the relative bioavailability of the group to which Example 3 was administered was 209.0% compared to that of the group to which the Comparative Example was administered, indicating a significant increase in the absorption rate of the drug. The maximum concentration ($C_{max}$) showed no significant difference between the groups to which the Comparative Example and Example 3 were administered, respectively.

The above results indicate that the expandable gastroretentive drug delivery device remained in the stomach for a sufficient period of time as intended for development and continuously released the drug. Thereby, it was confirmed that it is possible to overcome the limitations that were difficult to improve with a conventional sustained-release gastroretentive drug delivery method, and that compliance with medication and the convenience of administration may be increased by replacing the formulation, which had to be administered multiple times a day, with the once-a-day dosage device according to the present disclosure.

Experimental Example 6: Experiment on Control of Gastric Retention of Gastroretentive Drug Delivery Device Having Foldable Arm Structure A dissolution test was performed to measure the time taken for complete unfolding of the arm in the gastroretentive drug delivery device having a foldable arm structure produced in each of Examples 6 to 8 and to measure the time during which the arm is maintained in a maximally unfolded state. The dissolution test was performed in the 1.2 solution according to dissolution test method II of the general test method described in the Korean Pharmacopoeia. Conditions for the dissolution test are shown in Table 14 below. The results of the dissolution test are shown in Table 15 below.

TABLE 14

| Dissolution test method | Method II (paddle method) of general test method described in Korean Pharmacopoeia |
|---|---|
| Temperature | 37 ± 0.5° C. |
| Paddle rotation speed | 100 rpm |
| pH of dissolution medium | pH 1.2 |
| Volume of dissolution medium | 900 mL |

TABLE 15

|  | Example 6 | Example 7 | Example 8 |
|---|---|---|---|
| Time (sec) taken for complete unfolding of arm | 99 | 81 | 85 |
| Time (hr) during which arm was maintained in maximally unfolded state | 5.5 | 11.3 | 16.5 |

As shown in Table 15 above, it could be confirmed that the arm in the gastroretentive drug delivery device was quickly unfolded within 2 minutes depending on the assembly configuration and that the drug delivery device had no functional abnormality. In addition, it could be confirmed that the gastroretentive drug delivery device having a foldable arm structure could adjust the maintenance time of the arm in an unfolded state to 5 to 16 hours or more depending on the assembly configuration, and that there was no abnormality in maintaining the arm in the unfolded state.

Experimental Example 7: Dissolution Test for Gastroretentive Drug Delivery Device Having Foldable Arm Structure The dissolution test was performed in the 1.2 solution according to dissolution test method II of the general test method described in the Korean Pharmacopoeia. In the dissolution test for Examples 6 to 8, dissolution was examined according to the general test method described in the Korean Pharmacopoeia under the conditions shown in Table 14 above, and the riboflavin drug concentration of the dissolution medium was analyzed by HPLC-UV. Analysis conditions for riboflavin are shown in Table 16 below.

TABLE 16

| Instrument | |
|---|---|
| HPLC | Waters 2695 separations module (Waters, Milford, CA, USA) |
| UV detector | Waters 2996 photodiode array detector (Waters, Milford, CA, USA) |
| | HPLC conditions |
| Analysis column | Zorbax 300SB-C18, 5.0 μm, 4.6 × 250 mm (Agilent Technologies, Torrance, CA, USA) |
| Absorbance λ | 266 nm |
| Mobile phase | 10 mM sodium phosphate buffer: acetonitrile = 60:40 |
| Flow rate | 1 mL/min |
| Column oven temperature | 30° C. |
| Amount injected | 20 μL |

The results of the dissolution test are shown in FIG. 15.

As shown in FIG. 15, it could be confirmed that the time taken for 80% or more of riboflavin to be dissolved could be adjusted from 3 hours to 12 hours or more, and that there was no abnormality in controlling drug release in a state in which the arm was unfolded.

Experimental Example 8: Evaluation of Gastric Retention Ability of Gastroretentive Drug Delivery Device Having Foldable Arm Structure The gastroretentive drug delivery device having a foldable arm structure, produced in Example 6, was administered to beagle dogs, and then the gastric retention ability of the device was examined by X-ray photography with time. The results of the experiment are shown in FIG. 16.

(1) Experimental Animals

Six male beagle dogs (aged about 14 to 15 months; Covance Beagles, Orient Bio Jeongeup Center, Korea) were housed in stainless steel mesh breeding cages (895 mm (W)×795 mm (L)×765 mm (H)) at a density of one animal per cage during quarantine, acclimatization, administration and observation periods. One animal was selected based on feed intake and body weight and was used in the experiment. The experiment was conducted in Room No. 2 of the first animal breeding zone of Knotus Co., Ltd. under the following conditions: temperature: 23±3° C.; relative humidity: 55±15%; ventilation frequency: 10 or more times/hour; lighting time: 12 hours (lighting up at 8 am and turning off at 8 pm); and illumination density: 150 to 300 Lux. The animal used in the experiment was fasted for 12 hours or more before drug administration.

(2) Experimental Method

To the animal, the riboflavin gastroretentive drug delivery device produced in Example 6 was orally administered once. X-ray photography was performed at 0, 0.167, 0.5, 1, 2, 4, 6, 8, 12 and 24 hours, and the results are shown in FIG. 16.

As shown in FIG. 16, it was confirmed that, when the gastroretentive drug delivery device of Example 6 was administered to the beagle dog, the arm was unfolded as the immediate-release initiation portion (operator) produced in Production Example 5 was disintegrated within 10 minutes after administration, indicating that the drug delivery device had a gastric retention function. In addition, it was confirmed that the gastric retention function was maintained for 6 hours or more after administration. It was confirmed that, within 8 hours after administration, the arm was folded as the sustained-release supporter produced in Production Example 7 was disintegrated, and the gastric retention function of the drug delivery device was lost. These results are consistent with the results shown in Experimental Examples 6 and 7, and indicate that the gastroretentive drug delivery device remained in the stomach for a sufficient period of time as intended for development and continuously supplied the drug to the upper small intestine.

As described above, the gastroretentive drug delivery device according to the present disclosure may remain in the stomach for a long time by having the structure that allows the arm to be unfolded rapidly due to disintegration of the immediate-release portion therein. In addition, the gastric retention ability of the drug delivery device may be maintained by the structure of the arm which is unfolded while the sustained-release portion containing a pharmacologically active drug is dissolved slowly and continuously releases the drug, and the gastric retention ability may be lost by the structure that allows the arm to be detached or re-folded after complete dissolution of the sustained-release portion. Finally, the drug delivery device whose gastric retention function has been lost may be transferred to the small intestine and excreted. Therefore, the gastroretentive drug delivery device according to the present disclosure has excellent effects in that it can be produced and applied independently of the release properties and gastric retention properties of the drug.

The gastroretentive drug delivery device according to the present disclosure differs from conventional sustained-release formulations and/or gastroretentive drug delivery systems in that it may immediately exhibit gastric retention ability by expansion as the immediate-release portion in the capsule device is disintegrated quickly upon contact with gastric juice and, at the same time, the arm is unfolded, and in that the gastroretentive drug delivery device enables the pharmacologically active drug to rapidly reach the effective blood concentration as the immediate-release portion contains the pharmacologically active drug. In addition, the gastroretentive drug delivery device according to the present disclosure enables the arm to be maintained in an unfolded state until the sustained-release portion completely releases the drug, and the gastroretentive drug delivery device can achieve excellent gastric retention ability regardless of the stomach's internal environment.

The gastroretentive drug delivery device according to the present disclosure may be applied to various drugs, including a drug whose absorption is limited to the upper gastrointestinal tract, a drug which is degraded at the high pH of the small intestine, or a drug that acts in the stomach, and the gastroretentive drug delivery device may maintain the blood concentration of the drug at a constant concentration, improve the bioavailability of the drug, and increase the therapeutic effect of the drug. In addition, the gastroretentive drug delivery device according to the present disclosure may be designed to have various types and numbers of drug release windows. Accordingly, the gastroretentive drug delivery device according to the present disclosure makes it possible to easily adjust the gastric retention time of the drug delivery device, the release profile of the pharmacologically active drug, etc. by controlling the contact between the sustained-release portion and gastric juice depending on the purpose of gastric retention.

As described above, the present disclosure has been described with reference to various embodiments. Those of ordinary skill in the art to which the present disclosure pertains can understand that the present disclosure may be implemented in a modified form without departing from the essential characteristics of the present disclosure. Therefore, it should be understood that the disclosed embodiments are exemplary in all aspects and are not restrictive. The scope of the present disclosure is defined by the appended claims rather than the above description, and all differences within the scope equivalent thereto should be construed as being included in the present disclosure.

What is claimed is:

1. A gastroretentive drug delivery device comprising:
   a capsule body having a space formed therein;
   an arm moving part movable along a longitudinal direction within the capsule body;
   an elastic body positioned between one end of the capsule body and the arm moving part and acting to move the arm moving part in the longitudinal direction toward the other end of the capsule body;
   an arm support part movable along the longitudinal direction within the capsule body;
   a capsule cap configured to engage the other end of the capsule body;
   a rail formed along the longitudinal direction within the capsule body; and
   an arm configured to be unfolded by longitudinal movement of the arm moving part and move along the rail,
   wherein a disintegrable immediate-release formulation is positioned between the arm moving part and the arm support part, and a disintegrable sustained-release formulation is positioned between the arm support part and the capsule cap.

2. The gastroretentive drug delivery device of claim 1, wherein the arm comprises a rotating part extending from one end thereof, and the arm is unfolded by rotation with respect to the rotating part by longitudinal movement of the arm moving part.

3. The gastroretentive drug delivery device of claim 2, wherein the arm moving part rotates the arm while moving in the longitudinal direction toward the arm support part by disintegration of the immediate-release formulation, and the arm is unfolded perpendicularly to the capsule body when the arm moving part comes into contact with the arm support part by disintegration of the immediate-release formulation.

4. The gastroretentive drug delivery device of claim 3, wherein the contacted arm moving part and arm support part move the unfolded arm along the rail while moving in the longitudinal direction toward the capsule cap by disintegration of the sustained-release formulation, and the arm reaches a portion free of the capsule body free of the rail by disintegration of the sustained-release formulation and is detached from the capsule body.

5. The gastroretentive drug delivery device of claim 1, wherein each of the arm moving part, the arm support part and the capsule cap comprises a magnetic material for generating mutual attraction.

6. The gastroretentive drug delivery device of claim 5, wherein the arm moving part moves in the longitudinal direction toward the arm support part by an elastic force from the elastic body and attraction between the arm moving part and the arm support part upon disintegration of the immediate-release formulation, and the arm support part moves in the longitudinal direction toward the capsule cap by attraction between the arm support part and the capsule cap upon disintegration of the sustained-release formulation.

7. The gastroretentive drug delivery device of claim 1, further comprising one or more drug release windows formed in the capsule body.

8. The gastroretentive drug delivery device of claim 7, wherein the drug release windows are a pair of windows facing each other, which are formed in the capsule body.

9. The gastroretentive drug delivery device of claim 2, wherein the rotating part of the arm comprises a rotating shaft, and the arm is unfolded by rotation with respect to the rotating shaft by longitudinal movement of the arm moving part, and then moves along the rail through the rotating part.

10. The gastroretentive drug delivery device of claim 3, wherein the arm moving part comprises a bidirectional extension on a lateral side thereof facing the elastic body, and the extension of the arm moving part comes into contact with the rotating part of the perpendicularly unfolded arm through the lower end of the extension, so that the arm is maintained in the perpendicularly unfolded state.

11. The gastroretentive drug delivery device of claim 10, wherein the arm comprises an extension formed on the outside thereof so as to be adjacent to the end from which the rotating part extends, and the extension of the arm comes into contact with the outside of the extension of the arm moving part in a state in which the arm is unfolded perpendicularly, so that the arm is maintained in the perpendicularly unfolded state.

12. The gastroretentive drug delivery device of claim 1, wherein the rail is composed of a pair of rails formed within the capsule body, and the arm is composed of a pair of arms, which are fitted into the rails, respectively, and connected to the capsule body.

13. The gastroretentive drug delivery device of claim 1, wherein the rail is composed of two or more pairs of rails formed within the capsule body, and the arm is composed of two or more pairs of arms, which are fitted into the pairs of rails, respectively, and connected to the capsule body.

14. A method for manufacturing a gastroretentive drug delivery device, the method comprising steps of:
   providing a capsule body having a space formed therein;
   providing an elastic body positioned between one end of the capsule body and an arm moving part and acting to move the arm moving part in a longitudinal direction toward the other end of the capsule body;
   providing the arm moving part movable along the longitudinal direction within the capsule body;
   providing an arm configured to be unfolded by longitudinal movement of the arm moving part and to move along a rail;
   providing an arm support part movable along the longitudinal direction within the capsule body; and
   providing a capsule cap configured to engage the other end of the capsule body,
   wherein the rail is formed along the longitudinal direction within the capsule body, and
   wherein a disintegrable immediate-release formulation is positioned between the arm moving part and the arm support part, and a disintegrable sustained-release formulation is positioned between the arm support part and the capsule cap.

15. The method of claim 14, wherein the arm moving part rotates the arm with respect to a rotating shaft of the arm while moving in the longitudinal direction toward the arm support part by disintegration of the immediate-release formulation, and the arm is unfolded perpendicularly to the capsule body when the arm moving part comes into contact with the arm support part by disintegration of the immediate-release formulation.

16. The method of claim 15, wherein the contacted arm moving part and arm support part move the unfolded arm along the rail while moving in the longitudinal direction toward the capsule cap by disintegration of the sustained-release formulation, and the arm reaches a portion of the capsule body free of the rail by disintegration of the sustained-release formulation and is detached from the capsule body.

* * * * *